United States Patent
Isogai

(10) Patent No.: US 11,685,799 B2
(45) Date of Patent: Jun. 27, 2023

(54) COMPOSITE PARTICLES, METHOD OF PRODUCING COMPOSITE PARTICLES, DRY POWDER, AND MOLDING RESIN COMPOSITION

(71) Applicant: TOPPAN PRINTING CO., LTD., Tokyo (JP)

(72) Inventor: Takuya Isogai, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 296 days.

(21) Appl. No.: 16/915,364

(22) Filed: Jun. 29, 2020

(65) Prior Publication Data
US 2020/0332040 A1    Oct. 22, 2020

Related U.S. Application Data

(63) Continuation of application No. PCT/JP2018/048117, filed on Dec. 27, 2018.

(30) Foreign Application Priority Data

Jan. 5, 2018   (JP) .................................. 2018-000575
May 1, 2018   (JP) .................................. 2018-088428

(51) Int. Cl.
C08F 220/18          (2006.01)
C08F 2/22            (2006.01)
(Continued)

(52) U.S. Cl.
CPC .............. *C08F 220/18* (2013.01); *B05D 7/02* (2013.01); *C08F 2/22* (2013.01); *C08F 2/44* (2013.01); *C08F 212/36* (2013.01); *C09D 7/61* (2018.01); *C09D 7/69* (2018.01); *C09D 101/02* (2013.01); *B05D 2201/02* (2013.01);
(Continued)

(58) Field of Classification Search
CPC .. C08F 220/18; C08F 2/22; C08F 2/44; C08F 251/02
See application file for complete search history.

(56) References Cited

U.S. PATENT DOCUMENTS 5,489,469 A    2/1996  Kobayashi et al.
6,117,474 A    9/2000  Kamada et al.
(Continued)

FOREIGN PATENT DOCUMENTS

CN    103665398 A    3/2014
CN    104610703 A    5/2015
(Continued)

OTHER PUBLICATIONS

Sharma et al., "Silver Nanoparticle Anchored With Novel Cross-linked Interpenetrating Polymer Networks (IPNs) and its Antibacterial Activity," Polym. Compos., 2016, p. 70. (Year: 2016).*
(Continued)

*Primary Examiner* — Catherine S Branch
(74) *Attorney, Agent, or Firm* — Foley & Lardner LLP

(57) ABSTRACT

Composite particles comprising at least one type of polymer particles having surfaces that have thereon coatings formed of finely-disintegrated cellulose, with the polymer particles and the finely-disintegrated cellulose being inseparably bonded together.

21 Claims, 10 Drawing Sheets

(51) Int. Cl.
  *C08F 2/44* (2006.01)
  *C08F 251/02* (2006.01)
  *C09D 7/40* (2018.01)
  *C09D 7/61* (2018.01)
  *B05D 7/02* (2006.01)
  *C08F 212/36* (2006.01)
  *C09D 101/02* (2006.01)

(52) U.S. Cl.
  CPC ...... *B05D 2502/00* (2013.01); *B05D 2518/00* (2013.01); *C08J 2333/08* (2013.01); *C08J 2333/10* (2013.01)

(56) References Cited

U.S. PATENT DOCUMENTS

| | | | |
|---|---|---|---|
| 2007/0098843 | A1 | 5/2007 | Tomohira |
| 2012/0283363 | A1 | 11/2012 | Kumamoto et al. |
| 2014/0037816 | A1 | 2/2014 | Bakeev et al. |
| 2016/0144330 | A1 | 5/2016 | Wesner et al. |
| 2017/0058116 | A1* | 3/2017 | Ando .................. C09D 7/40 |
| 2020/0222404 | A1 | 7/2020 | Ge et al. |
| 2020/0332040 | A1 | 10/2020 | Isogai |

FOREIGN PATENT DOCUMENTS

| | | |
|---|---|---|
| CN | 105642345 A | 6/2016 |
| CN | 107129585 A | 9/2017 |
| CN | 107141387 A | 9/2017 |
| CN | 107823145 A | 3/2018 |
| CN | 107868161 A | 4/2018 |
| EP | 3 736 297 A1 | 11/2020 |
| JP | H107704 A | 1/1998 |
| JP | 2001-288273 A | 10/2001 |
| JP | 2005-281470 A | 10/2005 |
| JP | 2007-217557 A | 8/2007 |
| JP | 2008-001728 A | 1/2008 |
| JP | 2008-007646 A | 1/2008 |
| JP | 2010-216021 A | 9/2010 |
| JP | 2013-014741 A | 1/2013 |
| JP | 2013-185096 A | 9/2013 |
| JP | 2014-043566 A | 3/2014 |
| JP | 2015-067573 A | 4/2015 |
| JP | 2016-155897 A | 9/2016 |
| JP | 2017-061594 A | 3/2017 |
| JP | 2017-109946 A | 6/2017 |
| JP | 2017-114768 A | 6/2017 |
| JP | 2017-150117 A | 8/2017 |
| JP | 2017-192897 A | 10/2017 |
| JP | 2019-038949 A | 3/2019 |
| JP | 2019-073669 A | 5/2019 |
| KR | 100764625 B1 * | 10/2007 |
| KR | 20170123099 A | 11/2017 |
| WO | WO-2007/136086 A1 | 11/2007 |
| WO | WO-2009/112836 A2 | 9/2009 |
| WO | WO-2010/095574 A1 | 8/2010 |
| WO | WO-2013/042654 A1 | 3/2013 |
| WO | WO-2014/088072 A1 | 6/2014 |
| WO | WO-2017/219127 A1 | 12/2017 |
| WO | WO-2018/110245 A1 | 6/2018 |
| WO | WO-2018/176891 A1 | 10/2018 |

OTHER PUBLICATIONS

Jiao et al., "Synthesis and studies of poly(ethylene glycol dimethacrylate) microcapsule," Colloid Polym. Sci. (2016) 294:639-646. (Year: 2016).*
English machine translation of KR 10-0764625B1. (Year: 2007).*
Chinese Office Action, dated May 10, 2022 issued in corresponding Chinese Patent Application No. 201880084299.X (16 pages).
Cheng et al. "Effect of expanded graphite and carbon nanotubes on the thermal performance of stearic acid phase change materials," Journal of Materials Science 52: 12370-12379, 2017 (Year: 2017).
Google translation CN 101791437 A, printed 2022 (Year: 2022).
Li et al. "Cellulose nanofibers enable paraffin encapsulation and the formation of stable thermal regulation nanocomposites," Nano Energy 34:541-548, 2017 (Year: 2017).
International Searching Authority, "International Search Report," issued in connection with International Patent Application No. PCT/JP2019/018047, dated Jul. 23, 2019.
International Searching Authority, "Written Opinion," issued in connection with International Patent Application No. PCT/JP2019/018047, dated Jul. 23, 2019.
Liu et al. "Study of Pickering emulsion stabilized by sulfonated cellulose nanowhiskers extracted from sisal fiber," Colloid and Polymer Science 293:963-974, 2015 (Year: 2015).
Noguchi et al., "Complete nanofibrillation of cellulose prepared by phosphorylation," Cellulose, published on Jan. 7, 2017.
Okada et al. "Solvent-free formation of hydroxyapatite coated biodegradable particles via nanoparticle-stabilized emulsion route," Applied Surface Science 262:39-44, 2012 (Year:2012).
Zhang et al. "Nanoemulsions and Nanolatexes Stabilized by Hydrophobically Functionalized Cellulose Nanocrystals," Macromolecules 50:6032-6042, 2017 (Year: 2017).
Extended European Search Report dated Feb. 19, 2021 for corresponding European Patent Application No. 18898115.3.
Gruneberger Franziska et al: "Fibrillated 1,4-6,cellulose in heterophase polymerization of 9-12, 14 nanoscale poly(methyl methacrylate) spheres", Colloid & Polymer Science, Springer Verlag, Heidelberg, DE, vol. 294, No. 9, Jun. 11, 2016, pp. 1393-1403.
Kalashnikova I. et al: "New Pickering Emulsions stabilized by bacterial cellulose nanocrystals", Langmuir, American Chemical Society, US, vol. 27, No. 12, Jun. 21, 2011, pp. 7471-7479.
European Extended Search Report from EP 19792001.0 dated May 11, 2021, (11 pages).
Fufisawa, et al: "Synthesis of Nanocellulose-stabilized Polymer Microparticles", 24th Annual Meeting of the Cellulose Society of Japan, Jul. 1, 2017, pp. 17-18, (with English-language machine translation, 7 pages).
Liu, et al., "PMMA@SCNC composite microspheres prepared from pickering emulsion template as curcumin delivery carriers", Journal of Applied Polymer Science, (2018), (9 pages).
Office Action dated Dec. 13, 2021 issued in a corresponding Chinese Patent Application No. 201880084299.X, (14 pages).
Zhang, et al., "Cellulose nanofibril-reinforced biodegradable polymer composites obtained via a Pickering emulsion approach", Cellulose 24:3313-3322, (2017).
International Searching Authority, "International Search Report," issued in connection with International Patent Application No. PCT/JP2018/048117, dated Apr. 2, 2019.
International Searching Authority, "Written Opinion," issued in connection with International Patent Application No. PCT/JP2018/048117, dated Apr. 2, 2019.
Database WPI; Week 201830 Thomson Scientific; London, GB; AN 2018-24451M; XP002802807.
Database WPI; Week 201830 Thomson Scientific; London, GB; AN 2018-271342; XP002802806.
Extended European Search Report issued in related European Patent Application No. 19791773.5, dated May 7, 2021.
Extended European Search Report issued in related European Patent Application. No. 20817959.8, dated Jun. 29, 2022. (6 pages).
Office Action issued in related U.S. Appl. No. 17/010,121, dated Sep. 19, 2022.
Office Action issued in related Chinese Patent Application No. 2019800272562.2, dated Jan. 5, 2022 (11 pages).
Japanese Office Action issued in connection with JP Appl. Ser. No. 2019-106122 dated Mar. 22, 2023.

* cited by examiner

COMPOSITE PARTICLES, METHOD OF PRODUCING COMPOSITE PARTICLES, DRY POWDER, AND MOLDING RESIN COMPOSITION

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2018/048117, filed on Dec. 27, 2018, which is based upon and claims the benefit of priority to Japanese Patent Applications Nos. 2018-000575, filed on Jan. 5, 2018; and 2018-088428, filed May 1, 2018 the disclosures of which are all incorporated herein by reference in their entireties.

BACKGROUND

Technical Field

The present invention relates to finely-disintegrated cellulose/polymer composite particles, a method of producing finely-disintegrated cellulose/polymer composite particles, dry powder of finely-disintegrated cellulose/polymer composite particles, thermoplastic resin-containing composite particles, a method of producing thermoplastic resin-containing composite particles, and a molding resin composition comprising thermoplastic resin-containing composite particles.

Background Art

Recently, attempts have been actively made for using wood cellulose fibers as a new functional material by micronizing the fibers until at least one side of the structure of each fiber has a nanometer-order length.

For example, as disclosed in Patent Literature 1, repeating machine processing of wood cellulose by using a blender or a grinder, finely-disintegrated cellulose fibers, i.e., cellulose nanofibers (also termed CNF hereinafter) can be obtained. It is known that CNF obtained through this method has a minor axis diameter in the range of 10 nm to 50 nm and a major axis diameter in the range of 1 µm to 10 mm. This CNF, which weighs only ⅕ the weight of steel but is stronger 5 times or more than steel and has a large specific surface area of 250 m$^2$/g or more, is expected to be used as a resin reinforcement filler or an adsorbent.

Furthermore, active approaches have also been made for chemically treating wood cellulose fibers to facilitate micronization, and micronizing these fibers through machine processing with a low energy that is about the same as the energy used for a household mixer. The method of the chemical treatment mentioned above is not particularly limited but may preferably be a method in which an anionic functional group is introduced to cellulose fibers to facilitate micronization. Introduction of an anionic functional group to cellulose fibers may cause osmotic effects, allowing solvent to more easily enter between the microfibril structures of the cellulose, and may greatly reduce the energy required for micronizing the raw cellulose materials. The method of introducing the anionic functional group is not particularly limited. For example, the method disclosed in Non-Patent Literature 1 may be used. This method uses phosphate esterification treatment so that surfaces of finely-disintegrated cellulose fibers can be selectively esterified with phosphate. Patent Literature 2 discloses a method in which cellulose is reacted with monochloroacetic acid or sodium monochloroacetate in a highly concentrated aqueous alkaline solution, for carboxymethylation of the cellulose. Alternatively, cellulose may be directly reacted with a carboxylic anhydride compound, such as maleic acid or phthalic acid, gasified in an autoclave, to introduce carboxyl groups to the cellulose.

Also, another method is known in which 2, 2, 6, 6-tetramethylpiperidinyl-1-oxy radical (TEMPO), a relatively stable N-oxyl compound, is used as a catalyst to selectively oxidize surfaces of micronized fibers of cellulose (e.g. see Patent Literature 3). The oxidization reaction using TEMPO as a catalyst (TEMPO oxidization reaction) enables environmentally friendly chemical reformation in an aqueous system, at room temperature and at normal pressures. TEMPO oxidation reaction, when applied to wood cellulose, does not progress to the inside of the crystals, but can selectively convert alcoholic primary carbon of the cellulose molecular chains only on the crystal surfaces into carboxyl groups.

The carboxyl groups selectively introduced to the crystal surfaces by TEMPO oxidization cause osmotic effects with ionization thereof, due to which the wood cellulose is dispersed into cellulose microfibrils in the solvent to provide cellulose single nanofibers (also termed CSNF hereinafter). CSNF exhibits high dispersion stability derived from the carboxyl group on the surfaces. It is known that wood-derived CSNF obtained from wood by TEMPO oxidation reaction has a structure with a high aspect ratio where a minor axis diameter is about 3 nm and a major axis diameter is several tens of nanometers to several tens of micrometers, and accordingly that an aqueous dispersion liquid of CSNF or molding thereof has high transparency. Patent Literature 4 discloses that a laminate film obtained by applying and drying a CSNF dispersion liquid has barrier properties.

As mentioned above, cellulose nanofibers (CNF) that can be produced using various methods weigh only ⅕ the weight of steel but are stronger 5 times or more than steel and have a large specific surface area of 250 m$^2$/g or more. Therefore, for example, when kneaded as a filler with a resin, the resin is expected to reduce weight and increase strength. Furthermore, CNF has a low linear thermal expansion coefficient. Therefore, when CNF is dispersed in a resin, thermal dimensional stability of the resin can be improved. (E.g., see Patent Literature 6)

When practical use of CNF is concerned, there is an issue that an obtained CNF dispersion liquid unavoidably has a low solid content concentration in the range of about 0.1% to 5%. For example, transportation of a finely-disintegrated cellulose dispersion may be comparable to transportation of a large quantity of solvent. Accordingly, the transportation cost will be high and feasibility may be significantly impaired. In addition, when used as an additive for strengthening a resin, the low solid content concentration may impair addition efficiency. Furthermore, if water used as a solvent is immiscible with the resin, formation of a composite will be difficult. Furthermore, CNF, when handled in a water-containing state, may decompose and therefore may require refrigerated storage, preservative treatment or the like. This may lead to cost increase.

However, if the solvent is simply removed from the dispersion liquid of finely-disintegrated cellulose such as by thermal drying, the finely-disintegrated cellulose may aggregate, keratinize, or form a film, making it difficult to express stable performance as an additive. Furthermore, due to the low CNF solid content concentration, removal of the solvent by drying may require a large quantity of energy, which may be one factor impairing feasibility.

Since resins are inherently hydrophobic, it may be extremely difficult to disperse hydrophilic CNF into a hydrophobic resin. Furthermore, resins are usually thermoformed at a high temperature of 200° C. or more. In this regard, an attempt to simply dissolve and knead CNF into a resin may allow CNF to remain unmixed in the resin during kneading. Therefore, CNF may be thermally deteriorated and does not necessarily obtain desired strength properties.

Thus, handling CNF in the form of a dispersion liquid is a cause of impairing feasibility. Accordingly, it has been strongly desired to provide a new handling mode in which CNF can be more easily handled.

CNF or CSNF has also been studied from the perspective of giving them further functions. For example, a further function may be given to CSNF by using a carboxyl group on the surfaces thereof. Patent Literature 5 discloses that, in a state of being adsorbed to the carboxy group on the surfaces of CSNF, metal ions are reduced and precipitated to obtain a composite in which metal nanoparticles are supported on CSNF (metal nanoparticle-carrying CSNF). Patent Literature 5 discloses an example of using metal nanoparticle-carrying CSNF as a catalyst. Specifically, it is disclosed that, when metal nanoparticles can be stably dispersed in a state of having high specific surface area, catalytic activity is improved.

As described above, various studies have been made for developing high-functional materials which can give new functions to finely-disintegrated cellulose, including CNF or CSNF that is a carbon neutral material.

Various types of microparticles or microcapsules have been put into practice as functional materials in various fields. Usually, microparticles are micro-size particles of various polymers and have been used as fillers, spacers, abrasives or the like. Attempts to impart and develop further functions have been made by forming microcapsule structures by covering surfaces of microparticles with shells as core substances. Specifically, a functional material, such as a magnetic material, pharmaceutical, pesticide, fragrance, adhesive, enzyme, pigment or dye, may be incorporated into core substances and microencapsulated, so that the functional material can be protected, or release behavior can be controlled. The functional material may further be applied to the shells covering the core substances. For purposes of this application, coatings formed can be the shell.

In this regard, since micro-size particles generally have a high specific surface area and more easily aggregated, there is an issue of dispersion stability. Depending on usages, micro-size particles are required to have biodegradability or biocompatibility.

Thus, it has also been strongly desired to provide a new handling mode in which microparticles can be more easily handled.

CITATION LIST

[Patent Literature] Patent Literature 1 JP 2010-216021 A; Patent Literature 2 WO2014/088072; Patent Literature 3 JP 2008-001728 A; Patent Literature 4 WO2013/042654; Patent Literature 5 WO2010/095574; Patent Literature 6 JP 2008-7646 A.

[Non-Patent Literature] Non-Patent Literature 1: Noguchi Y, Homma I, Matsubara Y. Complete nanofibrillation of cellulose prepared by phosphorylation. Cellulose. 2017; 24:1295.10.1007/s10570-017-1191-3.

SUMMARY OF THE INVENTION

Technical Problem

The present invention has been made in light of the circumstances set forth above and firstly aims to provide a new and easier handling mode for cellulose nanofibers, while characteristics of the cellulose nanofibers are maintained.

Also, in light of the circumstances set forth above, the present invention secondly aims to provide composite particles comprising a thermoplastic resin and CNF which can be dehydrated using a simple and more easy method and which can more easily form a composite with a resin, a method of producing the composite particles, and a molding resin composition comprising the composite particles.

Solution to Problem

To solve the above issues, the present invention proposes the following solution.

Composite particles according to a first aspect of the present invention comprise at least one type of polymer particles having surfaces that have thereon coatings formed of finely-disintegrated cellulose. In the composite particles, the polymer particles and the finely-disintegrated cellulose are inseparably bonded together.

The finely-disintegrated cellulose may have crystal surfaces to which an anionic functional group has been introduced.

The coatings may comprise a functional component other than cellulose; the functional component may be metal microparticles of at least one metal or compounds thereof; the metal microparticles and the finely-disintegrated cellulose may be inseparably bonded together; and the metal microparticles may comprise at least one metal selected from gold, silver, platinum and palladium, or a compound thereof.

The polymer particles may be obtained by polymerizing a monomer having a vinyl group.

The polymer particles may be obtained by polymerizing a monomer having a (meth)acrylic group.

The polymer particles may be obtained by polymerizing a polyfunctional monomer having at least two polymerizable functional groups.

At least one of the polymerizable functional groups of the polyfunctional monomer may be a vinyl group.

At least one of the polymerizable functional groups of the polyfunctional monomer may be a (meth)acrylic group.

The polyfunctional monomer may be divinylbenzene.

A method of producing composite particles according to a second aspect of the present invention includes: a step 1A of defibrating raw cellulose materials in a solvent to obtain a dispersion liquid of finely-disintegrated cellulose; a step 2A of coating surfaces of polymerizable monomer droplets with the finely-disintegrated cellulose in the dispersion liquid to achieve stability as an emulsion; and a step 3A of polymerizing the polymerizable monomer droplets to obtain composite particles in which polymer particles are coated with the finely-disintegrated cellulose.

The method may further include a step 4A of providing a functional component other than cellulose to the finely-disintegrated cellulose on the surfaces of the composite particles.

The step 4A may comprise: a step of mixing the dispersion liquid with a solution comprising at least one type of metal ions to obtain a mixed solution; and a step of reducing the metal ions in the mixed solution to produce metal microparticles of at least one metal or a compound thereof, while compounding the metal microparticles with the finely-disintegrated cellulose on the surfaces of the composite particles.

A method of producing composite particles according to a third aspect of the present invention includes: a step 1A of defibrating raw cellulose materials in a solvent to obtain a dispersion liquid of finely-disintegrated cellulose; an auxiliary step 1A of compounding a functional component other than cellulose with the finely-disintegrated cellulose in the dispersion liquid; a step 2A of coating surfaces of polymerizable monomer droplets with the finely-disintegrated cellulose in the dispersion liquid to achieve stability as an emulsion; and a step 3A of polymerizing the polymerizable monomer droplets to obtain composite particles in which polymer particles are coated with the finely-disintegrated cellulose.

The auxiliary step 1A may include: a step of mixing the dispersion liquid with a solution comprising at least one type of metal ions to obtain a mixed solution; and a step of reducing the metal ions in the mixed solution to produce metal microparticles of at least one metal or a compound thereof, while compounding the metal microparticles with the finely-disintegrated cellulose.

A dry powder according to a fourth aspect of the present invention comprises the composite particles according to an aspect set forth above and has a solid content of 80% or more and 100% or less.

The polymer particles may be formed of a thermoplastic polymer.

The finely-disintegrated cellulose may have crystal surfaces to which an anionic functional group has been introduced.

The polymer particles may be obtained by polymerizing a monomer having a vinyl group.

The polymer particles may be obtained by polymerizing a monomer having a (meth)acrylic group.

The polymer particles may be obtained by polymerizing a monofunctional monomer having only one polymerizable functional group.

The monofunctional monomer may be styrene.

A method of producing composite particles according to a fifth aspect of the present invention includes: a step 1B of defibrating raw cellulose materials in a solvent to obtain a dispersion liquid of finely-disintegrated cellulose; a step 2B of coating surfaces of polymerizable monomer droplets with the finely-disintegrated cellulose in the dispersion liquid to achieve stability as an emulsion; a step 3B of controlling pH of the emulsion to 3.5 or less; and a step 4B of polymerizing the polymerizable monomer droplets in the emulsion to obtain composite particles in which polymer particles are coated with the finely-disintegrated cellulose.

The pH of the emulsion may be controlled to 10 or more in the step 4B.

A method of producing composite particles according to a sixth aspect of the present invention includes: a step 1B of defibrating raw cellulose materials in a solvent to obtain a dispersion liquid of finely-disintegrated cellulose; a step 2B of coating surfaces of polymerizable monomer droplets with the finely-disintegrated cellulose in the dispersion liquid to achieve stability as an emulsion; a step 3C of deoxygenating a system of the emulsion; and a step 4C of polymerizing the polymerizable monomer droplets in the emulsion, while maintaining a state of the system being deoxygenated, to obtain composite particles in which polymer particles are coated with the finely-disintegrated cellulose.

A dry powder according to a seventh aspect of the present invention comprises the composite particles according to an aspect set forth above and has a solid content of 80% or more.

Advantageous Effects of the Invention

The composite particles according to an aspect of the present invention set forth above can provide a new and more easy handling mode for cellulose nanofibers, while characteristics of the cellulose nanofibers are maintained.

The composite particles according to an aspect of the present invention set forth above can provide a new and more easy handling mode for cellulose nanofibers, while characteristics of the cellulose nanofibers are maintained, and can also provide a new function to the cellulose nanofibers.

The composite particles, the method of producing the composite particles, and the molding resin composition comprising the composite particles, according to an aspect of the present invention set forth above, can provide a new handling mode for CNF with which a resin can more easily form a composite with the CNF.

Also, according to an aspect of the present invention set forth above, there can be provided composite particles comprising a thermoplastic resin and CNF which can be dehydrated using a simple and more easy method and which can more easily form a composite with a resin, a method of producing the composite particles, and a molding resin composition comprising the composite particles.

DETAILED DESCRIPTION

Embodiments of the present invention will be described below with reference to the drawings. In the following description of the drawings to be referred, components identical with or similar to each other are given the same or similar reference signs. It should be noted that the drawings are only schematically illustrated, and thus the relationship between thickness and two-dimensional size of the components, and the thickness ratio between the layers, are not to scale. Therefore, specific thicknesses and dimensions should be understood in view of the following description. As a matter of course, dimensional relationships or ratios may be different between the drawings.

Further, the embodiments described below are merely examples of configurations for embodying the technical idea of the present invention. The technical idea of the present invention does not limit the materials, shapes, structures, arrangements, and the like of the components to those described below. The technical idea of the present invention can be modified variously within the technical scope defined by the claims.

First Embodiment

With reference to the drawings, a first embodiment of the present invention will be described.

<Finely-Disintegrated Cellulose/Polymer Composite Particles>

Figure 1:
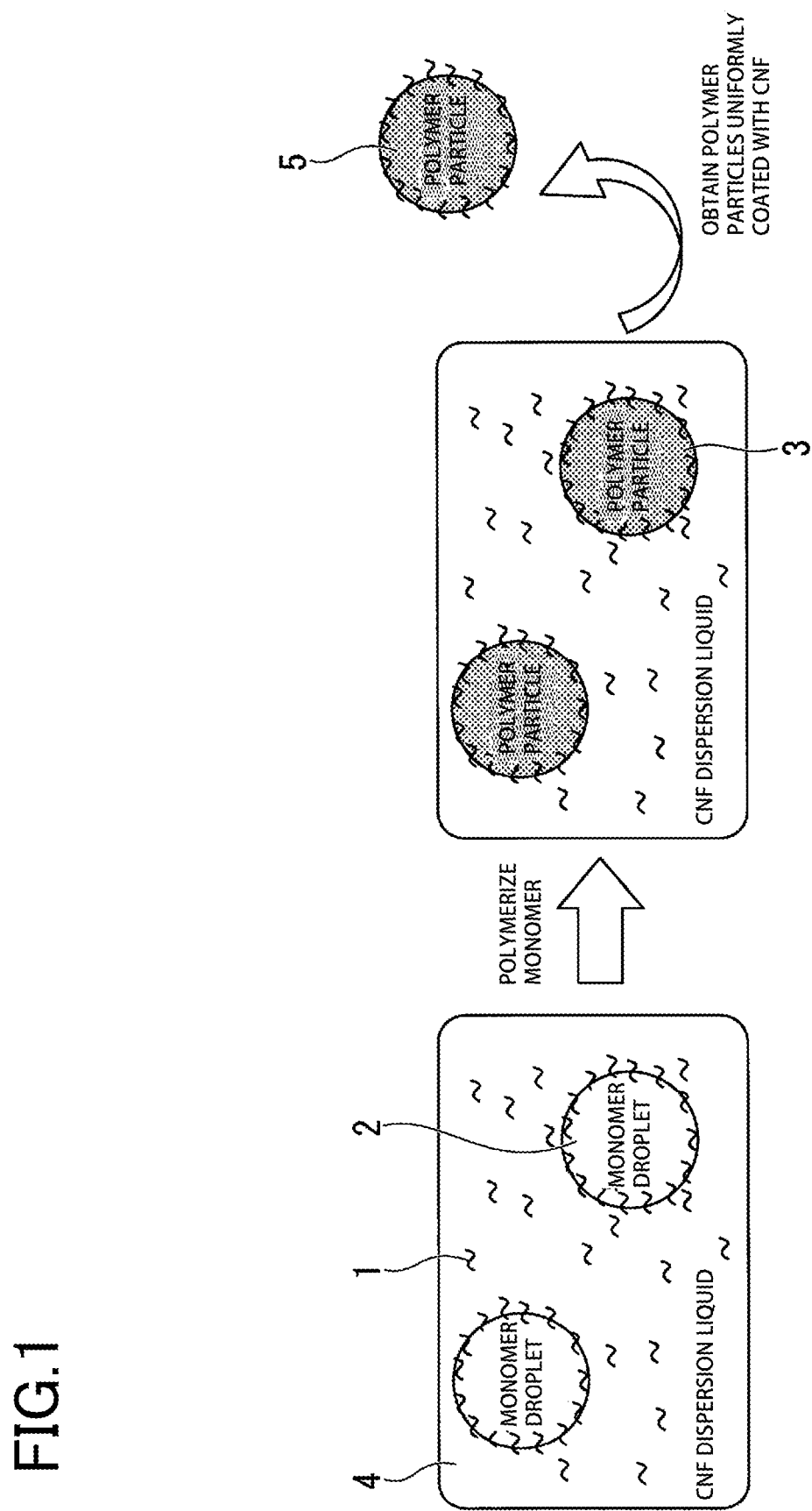
FIG. 1 is a schematic diagram illustrating an o/w Pickering emulsion using CNF, and composite particles obtained by polymerizing a polymerizable monomer in the emulsion, according to a first embodiment of the present invention.

First, composite particles 5 of finely-disintegrated cellulose/polymer particles according to a first embodiment of the present invention will be described. FIG. 1 is a schematic diagram illustrating an o/w Pickering emulsion using cellulose nanofibers (also termed CNF, cellulose or finely-disintegrated cellulose hereinafter) 1, and composite particles 5 obtained by polymerizing a polymerizable monomer in the emulsion.

The composite particles 5 include at least one type of polymer particles 3 each having a surface which is covered with a coating formed of the finely-disintegrated cellulose 1. The polymer particles 3 and the finely-disintegrated cellulose 1 are bonded together in an inseparable state to form composite particles.

As shown in FIG. 1, the cellulose 1 is adsorbed to the surfaces of monomer droplets 2 dispersed in a dispersion liquid 4 to stabilize an o/w Pickering emulsion. With the stabilized state being maintained, the monomer in the emulsion is polymerized to produce composite particles 5 using the emulsion as a template.

The term inseparable in the present and the subsequent embodiments refers to the state of polymer particles 3 coated with the finely-disintegrated cellulose 1 being maintained with no separation occurring between the finely-disintegrated cellulose 1 and the polymer particles 3 even after the dispersion liquid containing the composite particles 5 has been subjected to the following processing, i.e., processing in which the composite particles 5 are purified and washed by centrifugally treating the dispersion liquid, followed by removing the supernatant and adding a solvent for redispersion, or processing in which the composite particles 5 are repeatedly washed by a solvent through filtration washing using a membrane filter. The coated state can be confirmed by observing the surfaces of the composite particles 5 through a scanning electron microscope. The bonding mechanism between the finely-disintegrated cellulose 1 and the polymer particles 3 in the composite particles 5 is not known. However, it is assumed that due to formation of the composite particles 5 using an o/w emulsion as a template, which is stabilized by the finely-disintegrated cellulose 1, polymerization of the monomer progresses in a state in which the finely-disintegrated cellulose 1 is in contact with the monomer droplets 2 in the emulsion, and accordingly that the finely-disintegrated cellulose 1 is physically fixed to the polymerizing monomer, finally making the polymer particles 3 inseparable from the finely-disintegrated cellulose 1.

It should be noted that the term o/w emulsion refers to an oil-in-water emulsion in which oil in the form of oil droplets (oil particles) as a dispersion phase is dispersed in water as a continuous phase.

Since the composite particles 5 are produced using the o/w emulsion as a template, which has been stabilized by the finely-disintegrated cellulose 1, the composite particles 5 have a perfectly spherical shape derived from the o/w emulsion. Specifically, the composite particles 5 have a structure in which coatings of the finely-disintegrated cellulose 1 are formed on the surfaces of perfectly spherical polymer particles 3 and the coatings have a relatively uniform thickness. An average thickness of the coatings can be calculated through a process of fixing the composite particles 5 using an embedding resin, slicing the embedded composite particles 5 using a microtome, observing the slice through a scanning electron microscope, and measuring the thicknesses of 100 coatings at random appearing in the image of the sections of the composite particles 5. The composite particles 5 are preferred to be provided with coatings of a relatively uniform thickness. Specifically, the coatings are preferred to have a coefficient of variation of the thickness that is 0.5 or less, and more preferably 0.4 or less.

The finely-disintegrated cellulose 1 of the present embodiment is not particularly limited, but is preferred to have an anionic functional group on the crystal surfaces, and the content of the anionic functional group is preferred to be in the range of 0.1 mmol or more and 5.0 mmol or less per 1 g of cellulose.

Furthermore, the finely-disintegrated cellulose 1 is preferred to be a fibriform material derived from a microfibril structure. Specifically, the finely-disintegrated cellulose 1 is preferred to be a fibriform material and have a number average minor axis diameter in the range of 1 nm or more and 1,000 nm or less and a number average major axis diameter of 50 nm or more. It is also preferred that the number average major axis diameter is 5 times or more greater than the number average minor axis diameter. In addition, the finely-disintegrated cellulose 1 is preferred to have a crystal structure of cellulose type I.

<Method of Producing Composite Particles>

Next, a method of producing composite particles according to the present embodiment will be described.

The method of producing composite particles of the present embodiment include a step of defibrating raw cellulose materials in a solvent to obtain a dispersion liquid of finely-disintegrated cellulose (step 1A); a step of coating surfaces of polymerizable monomer droplets 2 with finely-disintegrated cellulose 1 in the dispersion liquid of finely-disintegrated cellulose to achieve stability as an emulsion (step 2A); and a step of polymerizing the polymerizable monomer droplets 2 to obtain composite particles 5 in which polymer particles 3 are coated with the finely-disintegrated cellulose 1 (step 3A).

The composite particles 5 obtained through the above production method are in the form of a dispersion. By removing solvent from the dispersion, composite particles 5 in the form of dry solids can be obtained. The method of removing solvent is not particularly limited. For example, excess water may be removed from the dispersion by centrifugation or filtration, followed by thermal drying using an oven to thereby obtain composite particles 5 in the form of dry solids. In this case, the obtained dry solids do not form a film or aggregate but are in the form of a fine-textured powder. The reason for this is not known. However, it is known that, usually, removal of solvent from a finely-disintegrated cellulose dispersion produces a firm aggregate of finely-disintegrated cellulose fibers or a film thereof.

In the case of a dispersion liquid containing composite particles 5, the composite particles each have a perfectly spherical shape and have surfaces to which the finely-disintegrated cellulose 1 is fixed. Therefore, it is considered that even if the solvent is removed, the composite particles are only brought into point contact with each other without causing finely-disintegrated cellulose 1 fibers to aggregate, and thus dry solids of the dispersion liquid containing composite particles 5 are obtained in the form of a fine-textured powder. The composite particles 5 obtained in the form of a dry powder without forming aggregate can be more easily redispersed into a solvent. Furthermore, even after redispersion, the redispersion liquid exhibits dispersion stability due to the finely-disintegrated cellulose 1 bonded to the surfaces of the composite particles 5.

The dry powder of composite particles 5, which is in the form of a dry powder, contains almost no solvent and can be redispersed into a solvent. Specifically, the solid content of the dry powder may be 80% or more, or 90% or more, or 95% or more. For example, the solid content of the dry powder of composite particles 5 may be 100%, i.e., may contain no solvent. Since solvent can be almost completely removed, the dry powder of composite particles 5 is advantageous from the perspective of reducing transportation cost, preventing decomposition, improving addition ratio or improving efficiency of kneading with a resin. If the composite particles have a solid content of 80% or more after being dried, the finely-disintegrated cellulose 1, which inherently tends to absorb moisture, may adsorb moisture from the air thereto, reducing the solid content over time. However, considering the technical idea of the present embodiment, i.e., the idea of more easily obtaining composite particles 5 in the form of a dry powder and redispersing the dry powder in a solvent, as long as the dry solids are obtained as a result of the process of achieving 80% or more and 100% or less solid content in dry powder including composite particles 5, the dry solids should be defined to be within the technical scope of the present embodiment.

Each step will be specifically described below.

(Step 1A)

In step 1A, raw cellulose materials are defibrated in a solvent to obtain a dispersion liquid of finely-disintegrated cellulose. First, various raw cellulose materials are dispersed in a solvent to obtain a suspension liquid. The raw cellulose materials in the suspension liquid are preferred to have a concentration that is 0.1% or more and less than 10%. If the concentration is less than 0.1%, the solvent quantity is excessive and thus productivity may be impaired. Therefore, this concentration is not favorable. If the concentration is 10% or more, viscosity of the suspension liquid may rapidly increase as the raw cellulose materials are defibrated, making it difficult to perform uniform defibration. Therefore, this concentration is not favorable. The solvent used for preparing a suspension liquid is preferred to contain 50% or more water. If the percentage of water in the suspension liquid is 50% or less, dispersion of the finely-disintegrated cellulose 1 may be hindered in the process of defibrating the raw cellulose materials in a solvent and obtaining a dispersion liquid of finely-disintegrated cellulose, which will be described later. Other than water, the solvent is preferred to contain a hydrophilic solvent. Hydrophilic solvents preferably include, but are not particularly limited to, alcohols such as methanol, ethanol and isopropanol; and cyclic ethers such as tetrahydrofuran. If necessary, pH of the suspension liquid may be controlled to enhance dispersibility of the cellulose or finely-disintegrated cellulose 1 to be produced. Aqueous alkaline solution used for controlling pH may be aqueous sodium hydroxide, aqueous lithium hydroxide, aqueous potassium hydroxide or aqueous ammonia solution, or an organic alkali, such as aqueous tetramethylammonium hydroxide solution, aqueous tetraethyl ammonium hydroxide solution, aqueous tetrabutylammonium hydroxide solution or aqueous benzyltrimethylammonium hydroxide solution, or other alkaline solutions. From the perspective of cost and the like, aqueous sodium hydroxide is preferred.

Next, the suspension liquid is physically defibrated to micronize the raw cellulose materials. The method of physical defibration is not particularly limited but may be a mechanical treatment using a high-pressure homogenizer, ultrahigh-pressure homogenizer, ball mill, roll mill, cutter mill, planetary mill, jet mill, attritor, grinder, blender, homomixer, ultrasonic homogenizer, nanogenizer, or underwater collision. Such physical defibration can micronize cellulose in the suspension liquid and can achieve a dispersion liquid in which the cellulose 1 has been micronized until at least one side of the cellulose structure has a nanometer-order length. In this case, depending on the time and the number of times of physical defibration, the number average minor axis diameter and the number average major axis diameter of the finely-disintegrated cellulose 1 obtained can be controlled.

Through the processing described above, a dispersion can be obtained in which the cellulose 1 has been micronized until at least one side of the cellulose structure has a nanometer-order length (dispersion liquid of finely-disintegrated cellulose). The obtained dispersion can be directly diluted or concentrated for use as a stabilizer for an o/w emulsion which will be described later.

As necessary, the finely-disintegrated cellulose dispersion may additionally comprise another component besides cellulose and the component used for pH control, without undermining the efficacy of the present invention. Such an additional component is not specifically limited but can be appropriately selected from known additives, depending on the usage or the like of the composite particles 5. Specifically, such an additional component may be an organometallic compound, such as alkoxysilane or a hydrolysate thereof; or an inorganic layered compound, inorganic needle-like mineral, defoaming agent, inorganic particles, organic particles, lubricant, antioxidant, antistatic agent, ultraviolet absorber, stabilizer, magnetic powder, orientation accelerator, plasticizer, cross-linker, magnetic material, pharmaceutical, pesticide, fragrance, adhesive, enzyme, pigment, dye, deodorant, metal, metal oxide, inorganic oxide or the like.

Usually, finely-disintegrated cellulose 1 is a fibriform material derived from a microfibril structure. The finely-disintegrated cellulose 1 used for the production method of the present embodiment is preferred to be a fibriform material satisfying the following conditions. Specifically, the finely-disintegrated cellulose 1 is preferred to be a fibriform material. The fibriform finely-disintegrated cellulose 1 may have a number average minor axis diameter in the range of 1 nm or more and 1,000 nm or less, and more preferably in the range of 2 nm or more and 500 nm or less. If the number average minor axis diameter is less than 1 nm, it may be difficult to obtain a rigid finely-disintegrated cellulose fiber structure having high crystallinity, and accordingly it may be difficult to stabilize the emulsion and undergo polymerization reaction using the emulsion as a template. If the number average minor axis diameter exceeds 1,000 nm, the size is too large to stabilize the emulsion and thus it is difficult to control the size and shape of the composite particles 5 to be obtained. The number average major axis diameter is not specifically limited, but is preferred to be 5 times or more greater than the number average minor axis diameter. If the number average major axis diameter is less than 5 times the number average minor axis diameter, the size and shape of the composite particles 5 cannot be sufficiently controlled, and thus this number average major axis diameter is unfavorable.

A number average minor axis diameter of finely-disintegrated cellulose fibers is obtained by measuring minor axis diameters (minimum diameters) of 100 fibers through transmission electron microscope observation and atomic force microscope observation, and calculating an average of the minor axis diameters of the measured 100 fibers. A number average major axis diameter of finely-disintegrated cellulose fibers is obtained by measuring major axis diameters (maximum diameters) of 100 fibers through transmission electron microscope observation and atomic force microscope observation, and calculating an average of the major axis diameters of the measured 100 fibers.

The type or the crystal structure of cellulose that can be used as raw materials of the finely-disintegrated cellulose 1 is not particularly limited. Specifically, for example, as a raw material composed of cellulose type I crystals, non-wood-based natural cellulose such as cotton linters, bamboo, hemp, bagasse, kenaf, bacterial cellulose, ascidian cellulose or valonia cellulose can be used, in addition to wood-based natural cellulose. Furthermore, regenerated cellulose can also be used, as represented by rayon fibers and cupra fibers composed of cellulose type II crystals. From the perspective of ease of availability, wood-based natural cellulose is preferred to be used as a raw material. Wood-based natural cellulose includes, but is not particularly limited to, cellulose generally used for producing cellulose nanofibers, such as softwood pulp, hardwood pulp and recycled waste-paper pulp. Wood-based natural cellulose is preferred to be softwood pulp because it is more easily purified and micronized.

Raw cellulose materials are preferred to be chemically modified. More specifically, it is preferred that an anionic functional group be introduced to the crystal surfaces of raw cellulose materials to be micronized.

This is because introduction of an anionic functional group to the crystal surfaces of cellulose may cause osmotic effects, allowing solvent to more easily enter between the cellulose crystals, and thus micronization of the raw cellulose materials may more easily progress.

The type of such an anionic functional group introduced to the crystal surfaces of cellulose or the method of introduction is not particularly limited. As to the type, a carboxyl group or a phosphate group is preferred. A carboxyl group is even more preferred due to ease of selective introduction to the crystal surfaces of cellulose.

The method of introducing a carboxyl group to the cellulose fiber surfaces is not particularly limited. Specifically, for example, cellulose may be reacted with monochloroacetic acid or sodium monochloroacetate in a high-concentration aqueous alkaline solution to achieve carboxymethylation. Alternatively, cellulose may be directly reacted with a carboxylic anhydride compound, such as maleic acid or phthalic acid, gasified in an autoclave, to introduce carboxyl groups to the cellulose. As another method, a co-oxidant may be used in the presence of an N-oxyl compound, such as TEMPO, which has high selectivity for oxidation of alcoholic primary carbon, under relatively mild conditions of aqueous systems, while the crystal structure of the cellulose is retained as much as possible. Oxidization using an N-oxyl compound is more preferred from the perspectives of selectivity for carboxyl-group introduction sites and reduction of environmental load.

The N-oxyl compound may be TEMPO (2,2,6,6-tetramethylpiperidine-1-oxy radical), 2,2,6,6-tetramethyl-4-hydroxypiperidine-1-oxyl, 4-methoxy-2,2,6,6-tetramethylpiperidine-N-oxyl, 4-ethoxy-2,2,6,6-tetramethylpiperidine-N-oxyl, 4-acetamide-2,2,6,6-tetramethylpiperidine-N-oxyl, or the like. Of these compounds, TEMPO is preferred due to having high reactivity. The amount of N-oxyl compound used is not particularly limited, but may be an amount for catalytic use. Typically, the amount is approximately 0.01 mass % to 5.0 mass % relative to the solid content of wood-based natural cellulose to be oxidized.

The oxidation method using an N-oxyl compound may, for example, be a method in which wood-based natural cellulose is dispersed in water and oxidized in the presence of the N-oxyl compound. In this method, a co-oxidant is preferred to be used together with the N-oxyl compound. In this case, in the reaction system, the N-oxyl compound is gradually oxidized by the co-oxidant to generate an oxammonium salt by which the cellulose is oxidized. In this oxidation treatment, oxidation reaction proceeds smoothly even under mild conditions, improving the efficiency of introducing a carboxyl group. When oxidation treatment is performed under mild conditions, the crystal structure of cellulose is likely to be maintained.

As the co-oxidant, any oxidant may be used, such as halogen, hypohalous acid, halous acid, perhalic acid or salts thereof, or halogen oxide, nitrogen oxide or peroxide, as long as the oxidation reaction can be promoted. From the perspectives of availability and reactivity, sodium hypochlorite is preferred. The amount of the co-oxidant used is not particularly limited as long as the oxidation reaction can be promoted. Typically, the amount is approximately 1 mass % to 200 mass % relative to the solid content of the wood-based natural cellulose to be oxidized.

At least one compound selected from the group consisting of bromides and iodides may be used together with an N-oxyl compound and a co-oxidant. Thus, the oxidation reaction can progress smoothly, improving the efficiency of introducing a carboxyl group. As such a compound, sodium bromide or lithium bromide is preferred, and sodium bromide is more preferred from the perspectives of cost and stability. The amount of the compound used is not particularly limited as long as the oxidation reaction can be promoted. Typically, the amount is approximately 1 mass % to 50 mass % relative to the solid content of the wood-based natural cellulose to be oxidized.

The temperature of the oxidization reaction is preferred to be 4° C. to 80° C., and more preferred to be 10° C. to 70° C. If the reaction temperature is less than 4° C., reactivity of the reagents may lower and thus the reaction time may increase. If the reaction temperature is more than 80° C., side reactions may accelerate and thus the molecular weight of the sample may be lowered. This may lead to collapse of the rigid finely-disintegrated cellulose fiber structure having high crystallinity, preventing use as a stabilizer for an o/w emulsion.

The reaction time of the oxidation treatment may be appropriately determined considering reaction temperature, desired amount of a carboxyl group, and the like, but may typically be about 10 minutes to 5 hours, although it is not particularly limited thereto.

During oxidation reaction, pH of the reaction system is not particularly limited but is preferred to be in the range of 9 to 11. If pH is 9 or higher, reaction may efficiently proceed. If pH is higher than 11, side reactions may progress and decomposition of the sample may be accelerated. During the oxidation treatment, pH in the reaction system unavoidably lowers with the progress of oxidation due to generation of a carboxyl group. Therefore, pH of the reaction system is preferred to be maintained in the range of 9 to 11 during the oxidation treatment. The method of maintaining pH of the reaction system in the range of 9 to 11 may be a method in which an aqueous alkaline solution is added to the reaction system in response to lowering of pH.

The aqueous alkaline solution may be aqueous sodium hydroxide, aqueous lithium hydroxide, aqueous potassium hydroxide or aqueous ammonia solution, or an organic alkali, such as aqueous tetramethylammonium hydroxide solution, aqueous tetraethyl ammonium hydroxide solution, aqueous tetrabutylammonium hydroxide solution or aqueous benzyltrimethylammonium hydroxide solution, or other alkaline solutions. From the perspective of cost and the like, aqueous sodium hydroxide is preferred.

The oxidation reaction using an N-oxyl compound can be stopped by adding alcohol to the reaction system. In this case, pH of the reaction system is preferred to be maintained to the above range (pH 9 to 11). As the alcohol to be added, a low-molecular-weight alcohol, such as methanol, ethanol or propanol, is preferred because the reaction is quickly stopped. However, ethanol is especially preferred from the perspective of safety or the like of secondary products generated by the reaction.

The reaction solution resulting from the oxidation reaction may be directly used in the micronization process. However, the oxidized cellulose contained in the reaction solution is preferred to be collected and washed with a washing liquid to remove catalysts such as the N-oxyl compound, impurities, and the like. The oxidized cellulose may be collected by a known method, such as filtration, using a glass filter or a nylon mesh having a pore diameter of 20 μm. The washing liquid used for washing the oxidized cellulose is preferred to be pure water.

When the obtained TEMPO-oxidized cellulose is defibrated, cellulose single nanofibers (CSNF) can be obtained with a uniform fiber width of 3 nm. When CSNF is used as a raw material of the finely-disintegrated cellulose 1 for composite particles 5, droplets of the obtained o/w emulsion are likely to have a uniform size due to the uniform structure of CSNF.

As described above, CSNF used in the present embodiment can be obtained through a process of oxidizing raw cellulose materials, and a process of micronizing the cellulose materials and dispersing the finely-disintegrated cellulose into a liquid. The content of a carboxyl group introduced to CSNF is preferred to be in the range of 0.1 mmol/g or more and 5.0 mmol/g or less, and is more preferred to be 0.5 mmol/g or more and 2.0 mmol/g or less. If the content of the carboxyl group is less than 0.1 mmol/g, osmotic effects do not necessarily occur between the cellulose microfibrils, disabling entry of solvent. Therefore, it may be difficult to micronize cellulose for uniform dispersion. If the content of the carboxyl group exceeds 5.0 mmol/g, the molecular weight of the cellulose microfibrils may be lowered due to side reactions of the chemical treatment. Therefore, a rigid finely-disintegrated cellulose fiber structure having high crystallinity cannot be necessarily achieved, and thus the cellulose cannot be used as a stabilizer for an o/w emulsion.

(Step 2A)

In step 2A, surfaces of the polymerizable monomer droplets 2 are coated with the finely-disintegrated cellulose 1 in a dispersion liquid of finely-disintegrated cellulose, for stabilization as an emulsion.

Specifically, a polymerizable monomer is added to the dispersion liquid of finely-disintegrated cellulose obtained in step 1A and dispersed therein in the form of droplets. Furthermore, surfaces of the polymerizable monomer droplets 2 are coated with finely-disintegrated cellulose 1 to thereby prepare an o/w emulsion stabilized by the finely-disintegrated cellulose 1.

The method of preparing an o/w emulsion is not particularly limited but a typical emulsification method, e.g., various methods using homogenizers or machine stirring methods, may be used. Specifically, the method may be a mechanical treatment using a high-pressure homogenizer, ultrahigh-pressure homogenizer, multipurpose homogenizer, ball mill, roll mill, cutter mill, planetary mill, jet mill, attritor, grinder, blender, homomixer, ultrasonic homogenizer, nanogenizer, or underwater collision. A plurality of mechanical treatments may be combined.

In the case of using an ultrasonic homogenizer, for example, a polymerizable monomer may be added to the dispersion liquid of finely-disintegrated cellulose obtained in step 1A to obtain a mixed solvent. Then, the tip of the ultrasonic homogenizer may be inserted into the mixed solvent to perform ultrasonic treatment. The conditions of treatment using an ultrasonic homogenizer are not particularly limited. However, for example, the frequency may be typically 20 kHz or more and the output may be typically 10 W/cm$^2$ or more. Duration of the treatment is not particularly limited but may typically be about 10 seconds to 1 hour.

Through the ultrasonic treatment, polymerizable monomer droplets 2 are dispersed in the dispersion liquid of finely-disintegrated cellulose to progress emulsification. Furthermore, the finely-disintegrated cellulose 1 is selectively adsorbed to the liquid/liquid interface between the monomer droplets 2 and the dispersion liquid of finely-disintegrated cellulose, so that the monomer droplets 2 are coated with the finely-disintegrated cellulose 1 and form a stabilized structure as an o/w emulsion. Thus, the emulsion stabilized with solids being adsorbed to the liquid/liquid interface is referred to as a Pickering emulsion. As mentioned above, the mechanism in which a Pickering emulsion is formed by finely-disintegrated cellulose fibers is not known. However, it is considered that, since cellulose has a hydrophilic site derived from a hydroxyl group and a hydrophobic site derived from a hydrocarbon group in the molecular structure thereof, i.e., has amphipathic nature, cellulose is adsorbed to the liquid/liquid interface between the hydrophobic monomer and the hydrophilic solvent, due to the amphipathic nature.

The o/w emulsion structure can be confirmed through optical microscope observation. Particle size in the o/w emulsion is not particularly limited but may typically be about 0.1 μm to 1,000 μm.

In the o/w emulsion structure, the thickness of the finely-disintegrated cellulose shell formed on the surface of each monomer droplet 2 is not particularly limited but may typically be about 3 nm to 1,000 nm. The thickness of the finely-disintegrated cellulose shell can be measured, for example, using a cryo-TEM.

Any type of polymerizable monomer may be used in step 2A as long as it is a monomer which has a structure including a polymerizable functional group, and which is in a liquid form at room temperature, is immiscible with water and can form a polymer (high-molecular-weight polymer) through a polymerization reaction. A polymerizable monomer has at least one polymerizable functional group. A polymerizable monomer having one polymerizable functional group is referred to as a monofunctional monomer. A polymerizable monomer having two or more polymerizable functional groups is referred to as a multifunctional monomer. The type of the polymerizable monomer is not particularly limited. For example, the polymerizable monomer may be a multifunctional monomer in which at least one of the polymerizable functional groups is a vinyl group, or in which at least one of the polymerizable functional groups is a (meth) acrylic group. The type of the polymerizable monomer is not particularly limited but may, for example, be a (meth)acrylic monomer, a vinyl monomer or the like. A polymerizable monomer having a cyclic ether structure such as an epoxy group or an oxetane structure (e.g., ε-caprolactone) may be used.

It should be noted that the term (meth)acrylate may refer to both acrylate and methacrylate.

Examples of monofunctional (meth)acrylic monomers include 2-hydroxyethyl (meth)acrylate, 2-hydroxypropyl (meth)acrylate, 2-hydroxybutyl (meth)acrylate, n-butyl (meth)acrylate, isobutyl (meth)acrylate, t-butyl (meth)acrylate, glycidyl (meth)acrylate, acryloylmorpholine, N-vinylpyrrolidone, tetrahydrofurfuryl acrylate, cyclohexyl (meth)acrylate, 2-ethylhexyl (meth)acrylate, isobornyl (meth)acrylate, isodecyl (meth)acrylate, lauryl (meth)acrylate, tridecyl (meth)acrylate, cetyl (meth)acrylate, stearyl (meth)acrylate, benzyl (meth)acrylate, 2-ethoxyethyl (meth) acrylate, 3-methoxybutyl (meth)acrylate, ethyl carbitol (meth)acrylate, phosphoric acid (meth)acrylate, ethylene oxide-modified phosphoric acid (meth)acrylate, phenoxy (meth)acrylate, ethylene oxide-modified phenoxy (meth) acrylate, propylene oxide-modified phenoxy (meth)acrylate, nonyl phenol (meth)acrylate, ethylene oxide-modified nonyl phenol (meth)acrylate, propylene oxide-modified nonyl phenol (meth)acrylate, methoxy diethylene glycol (meth)acrylate, methoxy polyethylene glycol (meth)acrylate, methoxy propylene glycol (meth)acrylate, 2-(meth)acryloyl oxyethyl-2-hydroxy propyl phthalate, 2-hydroxy-3-phenoxy propyl (meth)acrylate, 2-(meth)acryloyl oxyethyl hydrogen phthalate, 2-(meth)acryloyl oxypropyl hydrogen phthalate, 2-(meth)acryloyl oxypropyl hexahydro hydrogen phthalate, 2-(meth)acryloyl oxypropyl tetrahydro hydrogen phthalate, dimethylaminoethyl (meth)acrylate, trifluoroethyl (meth) acrylate, tetrafluoropropyl (meth)acrylate, hexafluoropropyl (meth)acrylate, octafluoropropyl (meth)acrylate, an adamantane derivative mono(meth)acrylate, such as adamantyl acrylate having a monovalent mono(meth)acrylate which is derived from 2-adamantane and adamantane diol, and other such monomers.

Examples of bifunctional (meth)acrylic monomers may include di(meth)acrylates, such as ethylene glycol di(meth) acrylate, diethylene glycol di(meth)acrylate, butanediol di(meth)acrylate, hexanediol di(meth)acrylate, nonanediol di(meth)acrylate, ethoxylated hexanediol di(meth)acrylate, propoxylated hexanediol di(meth)acrylate, diethylene glycol di(meth)acrylate, polyethylene glycol di(meth)acrylate, tripropylene glycol di(meth)acrylate, polypropylene glycol di(meth)acrylate, neopentyl glycol di(meth)acrylate, ethoxylated neopentyl glycol di(meth)acrylate, tripropylene glycol di(meth)acrylate, hydroxy pivalate neopentyl glycol di(meth)acrylate, and other such monomers.

Examples of tri- or-more functional (meth)acrylic monomers may include tri(meth)acrylate s, such as trimethylolpropane tri(meth)acrylate, ethoxylated trimethylolpropane tri(meth)acrylate, propoxylated trimethylolpropane tri (meth)acrylate, tris 2-hydroxyethyl isocyanurate tri(meth) acrylate and glycerin tri(meth)acrylate; tri-functional (meth) acrylate compounds, such as pentaerythritol tri(meth) acrylate, dipentaerythritol tri(meth)acrylate and ditrimethylolpropane tri(meth)acrylate; polyfunctional (meth)acrylate compounds having three or more functional groups, such as pentaerythritol tetra(meth)acrylate, ditrimethylolpropane tetra(meth)acrylate, dipentaerythritol tetra (meth)acrylate, dipentaerythritol penta(meth)acrylate, ditrimethylolpropane penta(meth)acrylate, dipentaerythritol hexa(meth)acrylate and ditrimethylolpropane hexa(meth) acrylate; polyfunctional (meth)acrylate compounds in which a part of each of these (meth)acrylates is replaced by an alkyl group or ε-caprolactone; and other such monomers.

For example, the monofunctional vinyl monomer is preferred to be a vinyl ether-vinyl ester- or aromatic vinyl-based monomer or, in particular, is preferred to be styrene or a styrene-based monomer that is a liquid immiscible with water at room temperature.

The (meth)acrylate of the monofunctional vinyl monomer may be methyl (meth)acrylate, ethyl (meth)acrylate, butyl (meth)acrylate, t-butyl (meth)acrylate, 2-ethylhexyl (meth) acrylate, lauryl (meth)acrylate, alkyl (meth)acrylate, tridecyl (meth)acrylate, stearyl (meth)acrylate, cyclohexyl (meth) acrylate, benzyl (meth)acrylate, isobornyl (meth)acrylate, glycidyl (meth)acrylate, tetrahydrofurfuryl (meth)acrylate, an aryl (meth)acrylate, diethylaminoethyl (meth)acrylate, trifluoroethyl (meth)acrylate, heptafluorodecyl (meth)acrylate, dicyclopentenyl (meth)acrylate, dicyclopentenyloxyethyl (meth)acrylate, tricyclodecanyl (meth)acrylate, or the like.

Monofunctional aromatic vinyl monomers may be styrene, α-methyl styrene, o-methyl styrene, m-methyl styrene, p-methyl styrene, ethyl styrene, isopropenyl toluene, isobutyltoluene, tert-butyl styrene, vinyl naphthalene, vinyl biphenyl, 1,1-diphenylethylene, and the like.

Multifunctional vinyl monomers may have a multifunctional group having unsaturated bonds, such as divinylbenzene. A liquid which is immiscible with water at room temperature is preferred.

Specifically, for example, multifunctional vinyl monomers may be (1) divinyls, such as divinyl benzene, 1,2,4-trivinylbenzene and 1,3,5-trivinylbenzene; (2) dimethacrylates, such as ethylene glycol dimethacrylate, diethylene glycol dimethacrylate, triethylene glycol dimethacrylate, polyethylene glycol dimethacrylate, 1,3-propylene glycol dimethacrylate, 1,4-butylene glycol dimethacrylate, 1,6-hexamethylene glycol dimethacrylate, neopentyl glycol dimethacrylate, dipropylene glycol dimethacrylate, polypropylene glycol dimethacrylate and 2,2-bis(4-methacryloxydiethoxyphenyl) propane; (3) trimethacrylates, such as trimethylolpropane trimethacrylate and triethylolethane trimethacrylate; (4) diacrylates, such as ethylene glycol diacrylate, diethylene glycol diacrylate, triethylene glycol diacrylate, polyethylene glycol diacrylate, 1,3-dipropylene glycol diacrylate, 1,4-dibutylene glycol diacrylate, 1,6-hexylene glycol diacrylate, neopentyl glycol diacrylate, dipropylene glycol diacrylate, polypropylene glycol diacrylate, 2,2-bis(4-acryloxypropoxyphenyl) propane and 2,2-bis(4-acryloxydiethoxyphenyl) propane; (5) triacrylates, such as trimethylolpropane triacrylate and triethylolethane triacrylate; (6) tetraacrylates, such as tetramethylolmethane tetraacrylate; and (7) other such monomers including, for example, tetramethylene bis(ethyl fumarate), hexamethylene bis(acrylamide), triallyl cyanurate and triallyl isocyanurate.

Specifically, for example, multifunctional styrene monomers may be divinylbenzene, trivinylbenzene, divinyltoluene, divinyl naphthalene, divinyl xylene, divinyl biphenyl, bis(vinylphenyl) methane, bis(vinylphenyl) ethane, bis(vinylphenyl) propane, bis(vinylphenyl) butane, and other such monomers.

Besides these monomers, materials that can used include, but are not limited to, a polyether resin, polyester resin, polyurethane resin, epoxy resin, alkyd resin, spiroacetal resin, polybutadiene resin, polythiolpolyene resin and the like, which have at least one polymerizable functional group.

These polymerizable monomers may be used singly or in combination of two or more.

The weight ratio between the dispersion liquid of finely-disintegrated cellulose fibers that can be used in step 2A and the polymerizable monomer is not particularly limited. It is preferred, however, that the polymerizable monomer is contained in the range of 1 part by mass or more and 50 parts by mass or less, relative to 100 parts by mass of the dispersion liquid of finely-disintegrated cellulose fibers. If the content of the polymerizable monomer is 1 part by mass or less, yield of the composite particles 5 may be lowered, which is not favorable. If the content exceeds 50 parts by mass, it may be difficult to uniformly coat the polymerizable monomer droplets 2 with the finely-disintegrated cellulose 1, which is not favorable.

The polymerizable monomer may contain a polymerization initiator in advance. Typically, a radical initiator, such as an organic peroxide or an azo polymerization initiator, is used as a polymerization initiator.

Examples of the organic peroxide include peroxyketals, hydroperoxides, dialkyl peroxides, diacyl peroxides, peroxycarbonates and peroxy esters.

The azo polymerization initiator may, for example, be ADVIN, AIBN or the like.

Examples of the azo polymerization initiator include 2,2-azobis(isobutyronitrile) (AIBN), 2,2-Azobis(2-methylbutyronitrile) (AMBN), 2,2-azobis(2,4-dimethylvaleronitrile) (ADVN), 1,1-azobis(1-cyclohexanecarbonitrile) (ACHN), dimethyl-2,2-azobisisobutyrate (MAIB), 4,4-azobis(4-cyanovaleric acid) (ACVA), 1,1-azobis(1-acetoxy-1-phenylethane), 2,2-azobis(2-methylbutyramide), azobis(4-methoxy-2,4-dimethylvaleronitrile), 2,2-azobis(2-methylamidinopropane) dihydrochloride, 2,2-azobis[2-(2-imidazolin-2-yl) propane], 2,2-azobis[2-methyl-N-(2-hydroxyethyl) propionamide], 2,2-azobis(2,4-trimethylpentane), 2-cyano-2-propylazoformamide, 2,2-azobis(N-butyl-2-methylpropionamide) and 2,2-azobis(N-cyclohexyl-2-methylpropionamide).

If a polymerizable monomer comprising a polymerization initiator in advance is used in step 2A, the polymerizable monomer droplets 2 in the emulsion droplets after formation of an o/w emulsion will comprise the polymerization initiator. Thus, when polymerizing the monomer in the emulsion in step 3A described later, the polymerization reaction may more easily progress.

The weight ratio between the polymerizable monomer that can be used in step 2A and a polymerization initiator is not particularly limited. It is preferred, however, that the polymerization initiator is contained by 0.1 parts by mass or more relative to 100 parts by mass polymerizable monomer. If the content of the polymerizable initiator is less than 0.1 parts by mass, the polymerization reaction does not necessarily sufficiently progress, and yield of the composite particles 5 lowers, which is unfavorable.

The polymerizable monomer may additionally contain in advance another functional component besides the polymerization initiator. Specifically, such an additional functional component may be, a magnetic material, pharmaceutical, pesticide, fragrance, adhesive, enzyme, pigment, dye, deodorant, metal, metal oxide, inorganic oxide or the like. If the polymerizable monomer additionally contains in advance another functional component besides a polymerization initiator, particles formed as composite particles 5 are permitted to contain this functional component therein so as to exhibit a function suitable for the usage.

(Step 3A)

In step 3A, the polymerizable monomer droplets 2 are polymerized to obtain composite particles 5 in which polymer particles 3 are coated with finely-disintegrated cellulose 1.

The method of polymerizing a polymerizable monomer is not particularly limited, but may be appropriately selected according to the type of the polymerizable monomer used and the type of the polymerization initiator used. For example, the method may be suspension polymerization.

The specific method of suspension polymerization is not particularly limited but may be a known method. For example, the o/w emulsion, prepared in step 2A, stabilized by coating the monomer droplets 2 comprising the polymerization initiator with the finely-disintegrated cellulose 1, may be heated while being stirred, for suspension polymerization. The method of stirring is not particularly limited but a known method may be used. Specifically, a disperser or a stirrer may be used. The o/w emulsion may only be heated without being stirred. The heating temperature may be appropriately determined according to the type of the polymerizable monomer and the type of the polymerization initiator, but is preferred to be in the range of 20° C. or more and 150° C. or less. If the heating temperature is less than 20° C., the reaction rate of polymerization may be lowered, which is unfavorable. If the heating temperature exceeds 150° C., the finely-disintegrated cellulose 1 may be modified, which is unfavorable. Polymerization reaction time may be appropriately determined according to the type of the polymerizable monomer and the type of the polymerization initiator, but may typically be about 1 hour to 24 hours. Polymerization reaction may be induced by irradiating the o/w emulsion with ultraviolet light which is a type of electromagnetic wave. Besides electromagnetic wave, a particle beam, such as an electron beam, may be used.

Through the above processing, perfectly spherical composite particles 5 can be prepared, in which polymer particles 3 are coated with finely-disintegrated cellulose 1.

Immediately after completion of polymerization reaction, the dispersion liquid of the composite particles 5 is in a state in which a large quantity of water is mixed with liberated finely-disintegrated cellulose 1 that has not contributed to formation of coatings for the composite particles 5.

Therefore, the prepared composite particles 5 are required to be collected and purified. The method of collection and purification is preferred to be centrifugal washing or filtration washing. The method of centrifugal washing may be a known method. Specifically, the composite particles 5 may be settled by centrifugation and the supernatant may be removed, followed by redispersing the settled composite particles 5 in a water-methanol mixed solvent. After repeating these processes, residual solvent may be removed from the sediment finally obtained by centrifugation to thereby collect the composite particles 5. The filtration washing may also be a known method. For example, the prepared composite particles 5 may be repeatedly subjected to suction filtration using a PTFE membrane filter having a pore size of 0.1 μm. After that, residual solvent may further be removed from the paste finally remaining on the membrane filter to thereby collect the composite particles 5.

The method of removing residual solvent is not particularly limited but may be air drying or thermal drying in an oven. The dry solids comprising the composite particles 5 obtained in this way do not form a film or aggregate but are in the form of a fine-textured powder.

Advantageous Effects of First Embodiment

The composite particles 5 of the present embodiment, which are derived from the finely-disintegrated cellulose 1 on the surfaces of the composite particles 5, are new composite particles having high biocompatibility and good dispersion stability without forming aggregate in a solvent.

The dry solids comprising the composite particles 5 of the present embodiment are obtained in the form of a fine-textured powder with no aggregate of the particles being formed. Therefore, the composite particles 5 obtained in the form of a dry powder can be more easily redispersed into a solvent. Even after redispersion, good dispersion stability is exhibited due to the coatings formed of CNF1 that has bonded to the surfaces of the composite particles 5.

The method of producing the composite particles 5 of the present embodiment is a method which imposes only low environmental load and can more easily provide new composite particles. The dry solids comprising composite particles of the finely-disintegrated cellulose 1 can be provided in the form enabling redispersion into a solvent.

The composite particles 5 of the present embodiment, from which almost all the solvent has been removed, are expected to reduce transportation cost, reduce decomposition, improve addition efficiency as an additive, or improve kneading efficiency for a hydrophobic resin.

The first embodiment of the present invention has been specifically described referring to the drawings. However, specific configurations of the present invention should not be limited to this embodiment but the present invention should include design changes and the like within the scope not departing from the spirit of the present invention. The components shown in the first embodiment and modifications thereof may be appropriately combined.

Second Embodiment

Next, a second embodiment of the present invention will be described. Composite particles 5B according to the present embodiment are different from the composite particles of the first embodiment in that a functional component other than cellulose is provided to the finely-disintegrated cellulose on the surfaces of the particles. In the following description, like reference signs designate common parts already described to omit duplicate description.

<Metal Nanoparticle-Carrying Finely-Disintegrated Cellulose/Polymer Composite Particles>

The composite particles (metal nanoparticle-carrying finely-disintegrated cellulose/polymer composite particles) 5B comprise a functional component, i.e., a metal, other than cellulose, in addition to the finely-disintegrated cellulose 1 on the surfaces of the composite particles 5 of the first embodiment.

The composite particles 5B can be obtained by directly forming metal microparticles (also termed nanoparticles hereinafter) by reduction and precipitation on the finely-disintegrated cellulose 1 that is present on the surfaces of the finely-disintegrated cellulose/polymer composite particles 5. The metal nanoparticles, which are directly formed by reduction and precipitation on the finely-disintegrated cellulose 1, are in a state of being inseparable from the finely-disintegrated cellulose 1.

The term inseparable in the present and the subsequent embodiments refers to the state, for example, of metal nanoparticles still being carried by the finely-disintegrated cellulose 1 even after the dispersion liquid containing the composite particles 5B has been subjected to the following processing, i.e., processing in which the composite particles 5B are purified and washed by centrifugally treating the dispersion liquid, followed by removing the supernatant and adding a solvent for redispersion, or processing in which the composite particles 5B are repeatedly washed by a solvent through filtration washing using a membrane filter. The carried state can be confirmed through surface observation of the metal nanoparticle-carrying finely-disintegrated cellulose/polymer composite particles 5B by means of a scanning electron microscope.

Metal nanoparticles which have been obtained by micronizing particles of metal or metal oxide so as to have a nanometer-order size are known to absorb and scatter light having a specific wavelength due to localized surface plasmon resonance (also termed LSPR hereinafter).

The shape of the metal nanoparticles is not particularly limited but may, for example, be a flat or rod shape. In particular, if the metal nanoparticles comprise gold or silver, or both, and if the metal nanoparticles have a flat shape, the wavelength of localized surface plasmon resonance can be widely controlled to be in the range of the visible region to near infrared region.

To maintain quantum size effects, metal nanoparticles are typically provided in the form of a dispersion liquid, i.e., in the state of being nanodispersed in a solvent. However, metal nanoparticles, due to having a large specific surface area, may more easily aggregate in a dispersion liquid, raising an issue of dispersion stability. If secondary particles are formed by aggregation, localized surface plasmon effects may be lost. This raises an issue that various additives are required to be used to prevent aggregation of metal nanoparticles, or an issue that solids concentration cannot be increased in the provided dispersion liquid of metal nanoparticles.

Thus, in the application of metal nanoparticles, it is also strongly desired that solvent is removed from the liquid dispersion to improve handleability as dry solids, as in the case of the dispersion liquid of finely-disintegrated cellulose. However, if solvent is completely removed from metal nanoparticles, the metal particles may form firm aggregate or may adhere to each other. This raises an issue that redispersion of the nanoparticles at a primary particle level may be difficult or an issue that the effects of localized surface plasmon resonance cannot be used after redispersion.

However, in composite particles 5B, metal nanoparticles are supported and fixed on the surfaces of the composite particles. Furthermore, the composite particles 5B have high dispersibility derived from the finely-disintegrated cellulose 1 on the surfaces of the composite particles. Therefore, composite particles 5B can be handled as a dry powder which can be more easily redispersed and which enables use of localized surface plasmon effects.

The composition of the metal nanoparticles is preferred to comprise, but is not particularly limited to, one or more metals selected from gold, silver, platinum and palladium, or a compound thereof. In the case of using a plurality of metals, for example, precipitated silver microparticles may be coated with a metal that is nobler than silver or a metal oxide, such as silica, to improve stability of the silver microparticles.

In the present embodiment, the term flat shape particles refers to substantially flat plate-shaped particles, i.e., particles having an average aspect ratio of 2.0 or more calculated by dividing an approximate particle size of the principal plane by an approximate particle thickness (approximate particle size/approximate particle thickness).

The particle size of the flat metal microparticles is preferred to be in the range of 20 nm to 1,000 nm. The particle thickness of the flat metal microparticles is preferred to be in the range of 5 nm to 100 nm, and more preferred to be in the range of 8 nm to 50 nm. The average aspect ratio (particle size/particle thickness) is preferred to be 2.0 or more, and more preferred to be in the range of 2.0 to 200.

As described above, the composite particles 5B of the present embodiment have coatings of finely-disintegrated cellulose 1 on the surfaces of respective polymer particles 3 which comprise at least one polymer. In the composite particles 5B, the polymer particles 3 and the finely-disintegrated cellulose 1 are inseparably bonded together, and the finely-disintegrated cellulose 1 comprises metal nanoparticles as a functional material.

<Method of Producing Composite Particles>

Next, a method of producing composite particles 5B of the present embodiment will be described. The method of producing composite particles 5B includes a step of providing metal nanoparticles as a functional component other than cellulose to the finely-disintegrated cellulose 1 on the surfaces of the composite particles 5 (step 4A), in addition to the step of defibrating raw cellulose materials in a solvent to obtain a dispersion liquid of finely-disintegrated cellulose (step 1A); the step of coating surfaces of polymerizable monomer droplets 2 with finely-disintegrated cellulose 1 in the dispersion liquid of finely-disintegrated cellulose to achieve stability as an emulsion (step 2A); and the step of polymerizing the polymerizable monomer to obtain composite particles 5 in which polymer particles 3 are coated with the finely-disintegrated cellulose 1 (step 3A).

The composite particles 5B, which are obtained in the form of a fine-textured dry powder, can be redispersed in a solvent. The composite particles 5B, which carry metal nanoparticles, can maintain the function of localized surface plasmon resonance derived from the metal nanoparticles even in the state of a dry powder or after being redispersed in a solvent.

Each step will be specifically described below.

(Steps 1A to 3A)

Steps 1A to 3A are the same as those of the first embodiment. In the present embodiment, an anionic functional group, such as a carboxyl group, is preferred to have been introduced to the surfaces of the cellulose fibers in step 1A because, in step 4A, metal is used as a functional component other than cellulose, i.e., metal nanoparticles are precipitated after reduction starting from the anionic functional group introduced to the surfaces of CSNF crystals as supports.

(Step 4A)

Then, in step 4A, metal nanoparticles as a functional component other than cellulose are provided to the finely-disintegrated cellulose 1 on the surfaces of the composite particles 5.

The method of providing metal nanoparticles to the finely-disintegrated cellulose 1 on the surfaces of the composite particles 5 is not particularly limited but a known method may be used.

For example, in a method that can be used, the composite particles 5 may be redispersed in water or a hydrophilic solvent to prepare a composite particle dispersion liquid, and metal nanoparticles may be added to the dispersion liquid of the composite particles 5.

Alternatively, in step 3A, the composite particle suspension liquid after completion of the polymerization reaction or the washing liquid used for the centrifugal washing process may be permitted to contain metal nanoparticles in advance.

As mentioned above, when compounding metal nanoparticles with the finely-disintegrated cellulose 1 on the surfaces of the composite particles 5, it is preferred that an anionic functional group is introduced in advance to the crystal surfaces of the finely-disintegrated cellulose 1. The following description explains details of a method of compounding metal nanoparticles with the composite particles 5 comprising anion-modified finely-disintegrated cellulose 1.

As a method of compounding metal nanoparticles with anion-modified finely-disintegrated cellulose on the surfaces of the composite particles 5, first, the composite particles 5 obtained in step 3A are redispersed in a hydrophilic solvent to obtain a composite particle dispersion liquid. The hydrophilic solvent is preferred to contain 50% or more water. Hydrophilic solvents other than water preferably include, but are not particularly limited to, alcohols such as methanol, ethanol and isopropanol; and cyclic ethers such as tetrahydrofuran. The method of redispersion is not particularly limited. For example, the powder solids of the composite particles 5 obtained in step 3A may be added to a hydrophilic solvent, followed by stirring using a stirrer or the like to more easily achieve redispersion.

Next, a solution comprising one or more types of metal ions is mixed with the composite particle dispersion liquid to obtain a mixed solution. Specifically, first, a metal or a compound comprising a metal is dissolved in a solvent, such as water, to prepare a solution comprising metal ions (metal ion-containing solution). The metal to be contained is preferred to be one or more metals selected from gold, silver, platinum and palladium, or a compound thereof but is not particularly limited thereto.

Next, while the composite particle dispersion liquid is stirred, the prepared metal ion-containing solution is gradually added thereto to obtain a mixed solution of the composite particle dispersion liquid and the metal ion-containing solution. In this case, since an anionic functional group has been introduced to the crystal surfaces of the finely-disintegrated cellulose on the surfaces of the composite particles 5, the metal ions in the mixed solution are adsorbed to the surfaces of the finely-disintegrated cellulose as counter ions for the anionic functional group.

Next, one or more types of metal ions in the mixed solution are reduced to produce metal nanoparticles of one or more metals or a compound thereof, while the metal nanoparticles form a composite with the finely-disintegrated cellulose 1. In this case, anisotropic growth of the metal nanoparticles may be accelerated to produce the metal nanoparticles into flat metal microparticles (metal nanoplates). In this case, metal nanoparticles are precipitated by reduction in a state in which the metal ions are adsorbed, as mentioned above, to the surfaces of the finely-disintegrated cellulose 1. Therefore, the metal nanoparticles are selectively formed by reduction and precipitation on the crystal surfaces of the finely-disintegrated cellulose 1 to thereby form a composite together with the finely-disintegrated cellulose 1. In this composite, the finely-disintegrated cellulose 1 and the metal nanoparticles are bonded together and are inseparable from each other.

The type of the aqueous solution comprising metal ions used for reduction is not particularly limited. For example, in the case of silver, an aqueous silver nitrate solution may be used. For example, in the case of gold, an aqueous chloroauric acid solution may be used. The reducing agent to be used is also not particularly limited. As the reducing agent, for example, ascorbic acid, citric acid, hydroquinone, sodium borohydride, sodium cyanoborohydride, dimethylamine borane, hydrazine or the like may be used. From the perspective of safety or cost, ascorbic acid, citric acid or sodium borohydride is preferred.

Silver nanoparticles or gold nanoparticles can absorb light of any wavelength ranging from the visible light to near infrared light depending on the particle size or the shape thereof, and thus can more easily provide desired optical characteristics according to usages.

In particular, the flat silver nanoparticles or flat gold nanoparticles can selectively absorb light of any wavelength ranging from the visible light to near infrared light by controlling the shape thereof, and thus can more easily provide desired optical characteristics according to usages of compositions.

In addition, if metal nanoparticles comprise silver which is inactive to the human body while being antimicrobial against various bacterial species, composite particles having good preservability and safety can be obtained.

In addition, since the composite formed of the finely-disintegrated cellulose 1 and silver is provided with antimicrobial properties, decay resistance of CSNF can also be improved. A plurality of metals other than silver may be used. In this case, precipitated silver nanoparticles may be coated with a metal nobler than silver or a metal oxide, such as silica, to improve stability of the silver nanoparticles.

If gold nanoparticles, which have good resistance to light, form a composite with the finely-disintegrated cellulose 1 on the surfaces of the composite particles, the composite can be used as a color material having high stability.

It should be noted that, to efficiently form metal nanoparticles by precipitation on the finely-disintegrated cellulose 1 on the surfaces of the composite particles 5, the total amount of the metal ions used for reduction and precipitation is preferred to be in the range of 0.0005 mmol or more to 0.4 mmol or less relative to 1 g of finely-disintegrated cellulose, more preferred to be in the range of 0.001 mmol or more and 0.2 mmol or less, and most preferred to be in the range of 0.002 mmol or more and 0.1 mmol or less.

Through the processing described above, a dispersion liquid of metal nanoparticle-carrying composite particles 5B can be obtained By removing solvent from the composite particles 5B, a dry powder of the metal nanoparticle-carrying composite particles 5B can be obtained. Solvent can be removed as in the method of removing solvent in step 3A from the composite particle dispersion liquid.

In step 4A described above, when compounding metal nanoparticles with the finely-disintegrated cellulose 1 on the surfaces of the composite particles 5, the concentration of the metal ions is not particularly limited. However, it is preferred that the concentration is controlled such that the amount of the metal ions in the dispersion liquid will be less than the amount of the anionic functional group that has been introduced to the finely-disintegrated cellulose 1 on the surfaces of the composite particles. If the amount of the metal ions in the dispersion liquid is more than the amount of the anionic functional group that has been introduced to the finely-disintegrated cellulose 1 on the surfaces of the composite particles, the composite particles may aggregate and uniform compounding is not necessarily achieved. The amount of the anionic functional group that has been introduced to the finely-disintegrated cellulose 1 on the surfaces of the composite particles may be calculated by a conductivity titration method.

In step 4A described above, when compounding metal microparticles with the finely-disintegrated cellulose 1 on the surfaces of the composite particles 5, concentration of the reducing agent in the mixed solution is not particularly limited, but is preferred to be controlled so as to be equal to or more than the concentration of the metal ions. This is because if the concentration of the reducing agent in the mixed solution is not more than the concentration of the metal ions, unreduced metal ions may remain in the mixed solution.

Advantageous Effects of Second Embodiment

According to the composite particles 5B of the present embodiment, advantageous effects similar to those of the first embodiment can be obtained. The composite particles 5B of the present embodiment have high biocompatibility and thus exhibit good dispersion stability without forming aggregate in solvent, which is derived from the finely-disintegrated cellulose 1 on the surfaces of the composite particles 5B. Furthermore, the composite particles 5B are new composite particles which have coatings formed of finely-disintegrated cellulose 1 and comprising metal nanoparticles as a functional component other than cellulose and thus are provided with functions derived from the metal nanoparticles.

The composite particles 5B of the present embodiment, which are obtained in the form of a fine-textured dry powder, can be redispersed in a solvent. The composite particles 5B, which carry metal nanoparticles, can maintain the function of localized surface plasmon resonance or the like derived from the metal nanoparticles even in the state of a dry powder or after being redispersed in a solvent.

The second embodiment of the present invention has been specifically described referring to the drawings. However, specific configurations of the present invention should not be limited to this embodiment but the present invention should include design changes and the like within the scope not departing from the spirit of the present invention. The components shown in the second embodiment and the following modifications may be appropriately combined.

(Modifications)

In step 4A of the above embodiment, a metal, as a functional component other than cellulose, has been provided to the finely-disintegrated cellulose 1 on the surfaces. However, the component other than cellulose is not particularly limited. For example, a functional material, such as a magnetic material, pharmaceutical, pesticide, fragrance, adhesive, enzyme, pigment, dye, deodorant, metal, metal oxide, inorganic oxide or the like may be used.

Third Embodiment

Next, a third embodiment of the present invention will be described. Composite particles 5C of the present embodiment, when compared to the composite particles 5B of the second embodiment, are different in that the production method does not include step 4A but that a functional component other than cellulose is directly provided to the finely-disintegrated cellulose 1 obtained in step 1A, followed by forming an emulsion. In the following description, like reference signs designate common parts already described to omit duplicate description.

<Method of Producing Composite Particles>

The method of producing composite particles 5C include a step of defibrating raw cellulose materials in a solvent to obtain a dispersion liquid of finely-disintegrated cellulose (step 1A); a step of producing a micronized-cellulose composite 1C by compounding a functional component other than cellulose with the finely-disintegrated cellulose 1 in the dispersion liquid of finely-disintegrated cellulose (auxiliary step 1A); a step of coating surfaces of polymerizable monomer droplets 2 with the micronized-cellulose composite 1C in the dispersion liquid of finely-disintegrated cellulose composite 1C to achieve stability as an emulsion (step 2A); and a step of polymerizing the polymerizable monomer to obtain composite particles 5C in which polymer particles are coated with the micronized-cellulose composite 1C (step 3A).

In the method of producing the composite particles 5C of the present embodiment, the functional component other than cellulose in auxiliary step 1A is a metal.

Each step will be specifically described below.

(Steps 1A to 3A)

Steps 1A to 3A are the same as those of the first embodiment except that the finely-disintegrated cellulose 1 is replaced by the micronized-cellulose composite 1C.

(Auxiliary Step 1A)

Auxiliary step 1A is performed between steps 1A and 2A.

In auxiliary step 1A, as in step 4A of the second embodiment, metal ions in a dispersion liquid containing the finely-disintegrated cellulose 1 are reduced and precipitated to produce metal crystals. Thus, metal nanoparticles form a composite with the finely-disintegrated cellulose 1, thereby obtaining a micronized-cellulose composite (finely-disintegrated cellulose/metal nanoparticles composite) 1C. The micronized-cellulose composite (finely-disintegrated cellulose/metal nanoparticles composite) 1C may be obtained by producing the anisotropic metal crystals during reduction and precipitation.

The process of obtaining the micronized-cellulose composite 1C may be appropriately selected from a known process described, for example, in Patent Literature 5 or the like set forth above.

Advantageous Effects of Third Embodiment

According to the composite particles 5C of the present embodiment, advantageous effects similar to those of the first embodiment can be obtained. The composite particles 5C have high biocompatibility and thus exhibit good dispersion stability, without forming aggregate in solvent, which is derived from the finely-disintegrated cellulose 1 on the surfaces of the composite particles 5C. Furthermore, the composite particles 5C are new composite particles which have coatings formed of the micronized-cellulose composite 1C and comprising metal nanoparticles as a functional component other than cellulose and thus are provided with functions derived from the metal nanoparticles.

The composite particles 5C of the present embodiment, which are obtained in the form of a fine texture dry powder, can be redispersed in a solvent. The micronized-cellulose composite 1C of the composite particles 5C, which carries metal nanoparticles, can maintain the function of localized surface plasmon resonance derived from the metal nanoparticles even in the state of a dry powder or after being redispersed in a solvent.

The third embodiment of the present invention has been specifically described referring to the drawings. However, specific configurations of the present invention should not be limited to this embodiment but the present invention should include design changes and the like within the scope not departing from the spirit of the present invention. The components shown in the third embodiment and the modifications may be appropriately combined.

(Modifications)

In auxiliary step 1A of the above embodiment, metal, as a functional component other than cellulose, has formed a composite with the finely-disintegrated cellulose 1. However, the component other than cellulose is not particularly limited. For example, a functional material, such as a magnetic material, pharmaceutical, pesticide, fragrance, adhesive, enzyme, pigment, dye, deodorant, metal, metal oxide, inorganic oxide or the like may be used.

Fourth Embodiment

Referring to the drawings, a fourth embodiment of the present invention will be described. In the drawings referred to below, like reference signs designate corresponding parts to omit repeated explanation as appropriate. The present embodiment is only an example of a configuration for specifying the technical idea of the present invention, and accordingly, materials, shapes, structures, arrangements, dimensions and the like of the individual parts should not be limited to those described below. The technical idea of the present invention can be modified variously within the technical scope defined in the claims.

<Finely-Disintegrated Cellulose/Thermoplastic Polymer Composite Particles>

Figure 7:
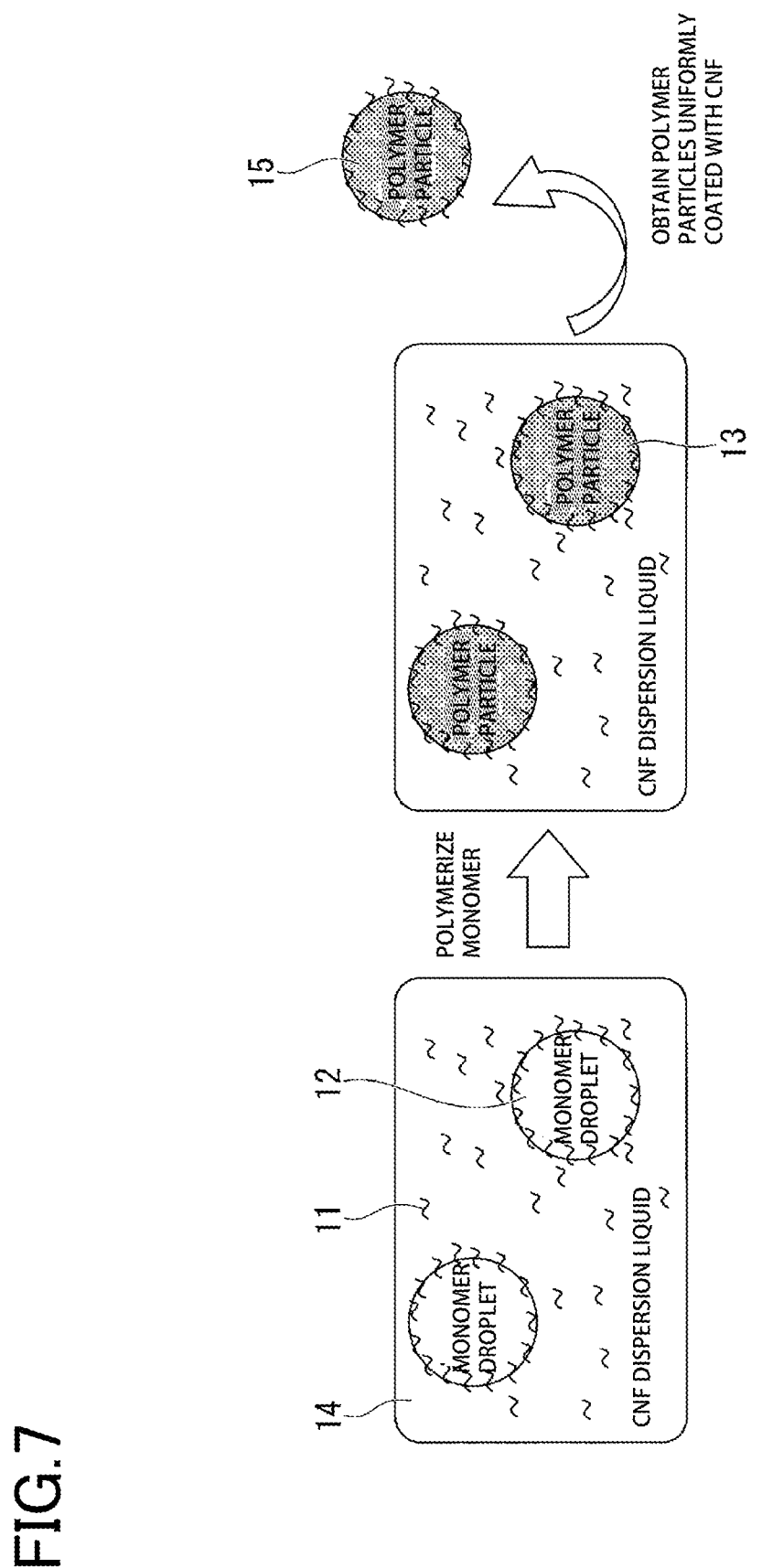
FIG. 7 is a schematic diagram illustrating an o/w Pickering emulsion using CNF, and thermoplastic resin/CNF composite particles obtained by polymerizing a polymerizable monomer in the emulsion, according to a fourth embodiment of the present invention.

First, composite particles 15 of finely-disintegrated cellulose/thermoplastic polymer particles, according to the fourth embodiment of the present invention will be described. FIG. 7 is a schematic diagram illustrating an o/w Pickering emulsion using cellulose nanofibers (also termed CNF, cellulose or finely-disintegrated cellulose hereinafter) 11, and composite particles 15 obtained by polymerizing a polymerizable monomer in the emulsion.

The composite particles 15 include at least one type of polymer particles 13 having surfaces covered with coatings formed of the finely-disintegrated cellulose 11. The polymer particles 13 and the finely-disintegrated cellulose 11 are inseparably bonded together to form composite particles.

As shown in FIG. 7, the cellulose 11 is adsorbed to the surfaces of monomer droplets 12 dispersed in a dispersion liquid 14 to stabilize the o/w Pickering emulsion. With the stabilized state being maintained, the monomer in the emulsion is polymerized to produce composite particles 15 using the emulsion as a template.

The term inseparable in the present and the subsequent embodiments refers to the state of each polymer particle 13 coated with the finely-disintegrated cellulose 11 still being maintained with no separation occurring between the finely-disintegrated cellulose 11 and the polymer particle 13 even after the dispersion liquid containing the composite particles 15 has been subjected to the following processing, i.e., processing in which the composite particles 15 are purified and washed by centrifugally treating the dispersion liquid, followed by removing the supernatant and adding a solvent for redispersion, or processing in which the composite particles 15 are repeatedly washed by a solvent through filtration washing using a membrane filter. The coated state can be confirmed by observing the surfaces of the composite particles 15 through a scanning electron microscope. The bonding mechanism between the finely-disintegrated cellulose 11 and the polymer particles 13 in the composite particles 15 is not known. However, it is assumed that due to formation of the composite particles 15 using the o/w emulsion as a template, which is stabilized by the finely-disintegrated cellulose 11, polymerization of the monomer progresses in a state in which the finely-disintegrated cellulose 11 is in contact with the monomer droplets 12 in the emulsion, and accordingly that the finely-disintegrated cellulose 11 is physically fixed to the polymerizing monomer, finally making the polymer particles 13 inseparable from the finely-disintegrated cellulose 11.

It should be noted that the term o/w emulsion refers to an oil-in-water emulsion in which oil in the form of oil droplets (oil particles) is dispersed using water as a continuous phase.

Since the composite particles 15 are produced using the o/w emulsion as a template, which has been stabilized by the finely-disintegrated cellulose 11, the composite particles 15 have a shape derived from the oil droplets of the o/w emulsion. Specifically, the composite particles 15 have a structure in which coatings of the finely-disintegrated cellulose 11 are formed on the surfaces of granular polymer particles 13 and the coatings have a relatively uniform thickness. An average thickness of the coatings is calculated through a process of fixing the composite particles 15 using an embedding resin, slicing the embedded composite particles 15 using a microtome, observing the slice through a scanning electron microscope, and measuring the thicknesses of 100 coatings at random appearing in the image of the sections of the composite particles 15. The composite particles 15 are preferred to be provided with coatings of a relatively uniform thickness. Specifically, the coatings are preferred to have a coefficient of variation of the thickness that is 0.5 or less, and more preferably 0.4 or less.

The finely-disintegrated cellulose 11 of the present embodiment is not particularly limited, but is preferred to have an anionic functional group on the crystal surfaces, and the content of the anionic functional group is preferred to be in the range of 0.1 mmol or more and 5.0 mmol or less per 1 g of cellulose.

Furthermore, the finely-disintegrated cellulose 11 is preferred to be a fibriform material derived from a microfibril structure. Specifically, the finely-disintegrated cellulose 11 is preferred to be a fibriform material and have a number average minor axis diameter in the range of 1 nm or more and 1,000 nm or less and a number average major axis diameter of 50 nm or more. It is also preferred that the number average major axis diameter is 5 times or more greater than the number average minor axis diameter. In addition, the finely-disintegrated cellulose 11 is preferred to have a crystal structure of cellulose type I.

<Method of Producing Composite Particles>

Next, a method of producing composite particles according to the present embodiment will be described. The method of producing composite particles of the present embodiment include a step of defibrating raw cellulose materials in a solvent to obtain a dispersion liquid of finely-disintegrated cellulose (step 1B); a step of coating surfaces of polymerizable monomer droplets 12 with finely-disintegrated cellulose 11 in the dispersion liquid of finely-disintegrated cellulose to achieve stability as an emulsion (step 2B); a step of controlling pH of the emulsion to 3.5 or less (step 3B); and a step of polymerizing the polymerizable monomer droplets 12 in the emulsion to obtain composite particles 15 in which polymer particles 13 are coated with the finely-disintegrated cellulose 11 (step 4B).

The composite particles 15 of the present embodiment obtained through the above production method are in the form of a dispersion. By removing solvent from the dispersion, composite particles 5 in the form of dry solids can be obtained. The method of removing solvent is not particularly limited. For example, excess water may be removed from the dispersion by centrifugation or filtration, followed by thermal drying using an oven to thereby obtain composite particles 5 in the form of dry solids. In this case, the obtained dry solids do not form a film or aggregate but are in the form of a fine-textured powder. The reason for this is not known. However, it is known that, usually, removal of solvent from a finely-disintegrated cellulose dispersion produces a firm aggregate of finely-disintegrated cellulose fibers or a film thereof. In the case of a dispersion liquid comprising composite particles 15, the composite particles have surfaces to which the finely-disintegrated cellulose 11 is fixed. Therefore, it is considered that even if the solvent is removed, the composite particles are only brought into point contact with each other without causing finely-disintegrated cellulose 11 fibers to aggregate, and thus dry solids of the composite particles 15 are obtained in the form of a fine-textured powder. The composite particles 15 obtained in the form of a dry powder without forming aggregate can be more easily redispersed into a solvent. Furthermore, even after redispersion, the redispersion liquid exhibits dispersion stability which is derived from the finely-disintegrated cellulose 11 that is bonded to the surfaces of the composite particles 15.

The dry powder of composite particles 15, which is in the form of dry solids, contains almost no solvent and can be redispersed into a solvent. Specifically, solid content of this dry powder can be 80% or more, or 90% or more, or 95% or more. Since solvent can be almost completely removed, the dry powder of composite particles 5 is advantageous from the perspective of reducing transportation cost, preventing decomposition, improving addition ratio or improving efficiency of kneading with a resin. If the composite particles have a solid content of 80% or more after being dried, the finely-disintegrated cellulose 11, which inherently tends to absorb moisture, may absorb moisture from the air, reducing the solid content over time. However, considering the technical idea of the present and the subsequent embodiments, i.e., the idea of more easily obtaining composite particles 15 in the form of a dry powder and redispersing the dry powder in a solvent, as long as the dry solids are obtained as a result of the process of achieving 80% or more solid content in the dry powder comprising composite particles 15, the dry solids should be defined to be within the technical scope of the present and the subsequent embodiments. The dry powder can be dehydrated using a simple and more easy method without forming aggregate. Also, in the dry powder, a thermoplastic resin has formed a composite with CNF in micro-size order and therefore the composite particles 15 can be favorably used as a molding resin composition.

Each step will be specifically described below.

(Step 1B)

In step 1B, raw cellulose materials are defibrated in a solvent to obtain a dispersion liquid of finely-disintegrated cellulose. First, various raw cellulose materials are dispersed in a solvent to obtain a suspension liquid. The raw cellulose materials in the suspension liquid are preferred to have a concentration that is 0.1% or more and less than 10%. If the concentration is less than 0.1%, the solvent quantity is excessive and thus productivity may be impaired. Therefore, this concentration is not favorable. If the concentration is 10% or more, viscosity of the suspension liquid may rapidly increase as the raw cellulose materials are defibrated, making it difficult to perform uniform defibration. Therefore, this concentration is not favorable. The solvent used for preparing a suspension liquid is preferred to contain 50% or more water. If the percentage of water in the suspension liquid is 50% or less, dispersion of the finely-disintegrated cellulose 11 may be hindered in the process of defibrating the raw cellulose materials in a solvent and obtaining a dispersion liquid of finely-disintegrated cellulose, which will be described later. Other than water, the solvent is preferred to contain a hydrophilic solvent. Hydrophilic solvents preferably include, but are not particularly limited to, alcohols such as methanol, ethanol and isopropanol; and cyclic ethers such as tetrahydrofuran. If necessary, pH of the suspension liquid may be controlled to enhance dispersibility of the cellulose or finely-disintegrated cellulose 11 to be produced. Aqueous alkaline solution used for controlling pH may be aqueous sodium hydroxide, aqueous lithium hydroxide, aqueous potassium hydroxide or aqueous ammonia solution, or an organic alkali, such as aqueous tetramethylammonium hydroxide solution, aqueous tetraethyl ammonium hydroxide solution, aqueous tetrabutylammonium hydroxide solution or aqueous benzyltrimethylammonium hydroxide solution, or other alkaline solutions. From the perspective of cost and the like, aqueous sodium hydroxide is preferred.

Next, the suspension liquid is physically defibrated to micronize the raw cellulose materials. The method of physical defibration is not particularly limited but may be a mechanical treatment using a high-pressure homogenizer, ultrahigh-pressure homogenizer, ball mill, roll mill, cutter mill, planetary mill, jet mill, attritor, grinder, blender, homomixer, ultrasonic homogenizer, nanogenizer, or underwater collision. Such physical defibration can micronize cellulose in the suspension liquid and can achieve a dispersion liquid in which the cellulose 11 has been micronized until at least one side of the cellulose structure has a nanometer-order length. In this case, depending on the time and the number of times of physical defibration, the number average minor axis diameter and the number average major axis diameter of the finely-disintegrated cellulose 11 to be obtained can be controlled.

Through the processing described above, a dispersion can be obtained in which the cellulose 11 has been micronized until at least one side of the cellulose structure has a nanometer-order length (dispersion liquid of finely-disintegrated cellulose). The obtained dispersion can be directly diluted or concentrated for use as a stabilizer for an o/w emulsion which will be described later.

As necessary, the finely-disintegrated cellulose dispersion may additionally comprise another component besides cellulose and the component used for pH control, without undermining the efficacy of the present invention. Such an additional component is not specifically limited but can be appropriately selected from known additives, depending on the usage or the like of the composite particles 15. Specifically, such an additional component may be an organometallic compound, such as alkoxysilane or a hydrolysate thereof; or an inorganic layered compound, inorganic needle-like mineral, defoaming agent, inorganic particles, organic particles, lubricant, antioxidant, antistatic agent, ultraviolet absorber, stabilizer, magnetic powder, orientation accelerator, plasticizer, cross-linker, magnetic material, pharmaceutical, pesticide, fragrance, adhesive, enzyme, pigment, dye, deodorant, metal, metal oxide, inorganic oxide or the like.

Usually, finely-disintegrated cellulose 11 is a fibriform material derived from a microfibril structure. The finely-disintegrated cellulose 11 used for the production method of the present embodiment is preferred to be a fibriform material satisfying the following conditions. Specifically, the finely-disintegrated cellulose 11 is preferred to be a fibriform material. The fibriform finely-disintegrated cellulose 11 may have a number average minor axis diameter in the range of 1 nm or more and 1,000 nm or less, and more preferably in the range of 2 nm or more and 500 nm or less. If the number average minor axis diameter is less than 1 nm, it may be difficult to obtain a rigid finely-disintegrated cellulose fiber structure having high crystallinity, and accordingly it may be difficult to stabilize the emulsion and undergo polymerization reaction using the emulsion as a template. If the number average minor axis diameter exceeds 1,000 nm, the size is too large to stabilize the emulsion and thus it is difficult to control the size and shape of the composite particles 15 to be obtained. The number average major axis diameter is not specifically limited, but is preferred to be 5 times or more greater than the number average minor axis diameter. If the number average major axis diameter is less than 5 times the number average minor axis diameter, the size and shape of the composite particles 15 cannot be sufficiently controlled, and thus this number average major axis diameter is unfavorable.

A number average minor axis diameter of finely-disintegrated cellulose fibers is obtained by measuring minor axis diameters (minimum diameters) of 100 fibers through transmission electron microscope observation and atomic force microscope observation, and calculating an average of the minor axis diameters of the measured 100 fibers. A number average major axis diameter of finely-disintegrated cellulose fibers is obtained by measuring major axis diameters (maximum diameters) of 100 fibers through transmission electron microscope observation and atomic force microscope observation, and calculating an average of the major axis diameters of the measured 100 fibers.

The type or the crystal structure of cellulose that can be used as raw materials of the finely-disintegrated cellulose 11 is also not particularly limited. Specifically, for example, as a raw material composed of cellulose type I crystals, non-wood-based natural cellulose such as cotton linters, bamboo, hemp, bagasse, kenaf, bacterial cellulose, ascidian cellulose or valonia cellulose can be used, in addition to wood-based natural cellulose. Furthermore, regenerated cellulose can also be used, as represented by rayon fibers and cupra fibers composed of cellulose type II crystals. From the perspective of ease of availability, wood-based natural cellulose is preferred to be used as a raw material. Wood-based natural cellulose includes, but is not particularly limited to, cellulose generally used for producing cellulose nanofibers, such as softwood pulp, hardwood pulp and recycled waste-paper pulp. From the perspective of ease of purification and micronization, softwood pulp is preferred.

Raw cellulose materials are preferred to be chemically modified. More specifically, it is preferred that an anionic functional group be introduced to the crystal surfaces of raw cellulose materials to be micronized.

This is because introduction of an anionic functional group to the crystal surfaces of cellulose may cause osmotic effects, allowing solvent to more easily enter between cellulose crystals and thus micronization of the raw cellulose materials may more easily progress. Furthermore, major axis diameters and the minor axis diameters of the finely-disintegrated cellulose can be more easily controlled. If the major and minor axis diameters of the finely-disintegrated cellulose can be more easily controlled, the size of the emulsion particles can be more easily controlled in step 2B. Resultantly, composite particles of a uniform size can be favorably obtained.

The type of such an anionic functional group introduced to the crystal surfaces of cellulose or the method of introduction is not particularly limited. As to the type, a carboxyl group or a phosphate group is preferred. A carboxyl group is even more preferred due to ease of selective introduction to the crystal surfaces of cellulose.

The method of introducing a carboxyl group to the cellulose fiber surfaces is not particularly limited. Specifically, for example, cellulose may be reacted with monochloroacetic acid or sodium monochloroacetate in a high-concentration aqueous alkaline solution to achieve carboxymethylation. Alternatively, cellulose may be directly reacted with a carboxylic anhydride compound, such as maleic acid or phthalic acid, gasified in an autoclave, to introduce carboxyl groups to the cellulose. As another method, a co-oxidant may be used in the presence of an N-oxyl compound, such as TEMPO, which has high selectivity for oxidation of alcoholic primary carbon, under relatively mild conditions of aqueous systems, while the crystal structure of the cellulose is retained as much as possible. Oxidization using an N-oxyl compound is more preferred from the perspectives of selectivity for carboxyl-group introduction sites and reduction of environmental load.

The N-oxyl compound may be TEMPO (2,2,6,6-tetramethylpiperidine-1-oxy radical), 2,2,6,6-tetramethyl-4-hydroxypiperidine-1-oxyl, 4-methoxy-2,2,6,6-tetramethylpiperidine-N-oxyl, 4-ethoxy-2,2,6,6-tetramethylpiperidine-N-oxyl, 4-acetamide-2,2,6,6-tetramethylpiperidine-N-oxyl, or the like. Of these compounds, TEMPO is preferred due to having high reactivity. The amount of N-oxyl compound used is not particularly limited, but may be an amount for catalytic use. Typically, the amount is approximately 0.01 mass % to 5.0 mass % relative to the solid content of wood-based natural cellulose to be oxidized.

The oxidation method using an N-oxyl compound may, for example, be a method in which wood-based natural cellulose is dispersed in water and oxidized in the presence of the N-oxyl compound. In this method, a co-oxidant is preferred to be used together with the N-oxyl compound. In this case, in the reaction system, the N-oxyl compound is gradually oxidized by the co-oxidant to generate an oxammonium salt by which the cellulose is oxidized. In this oxidation treatment, oxidation reaction proceeds smoothly even under mild conditions, improving the efficiency of introducing a carboxyl group. When oxidation treatment is performed under mild conditions, the crystal structure of cellulose is likely to be maintained.

As the co-oxidant, any oxidant may be used, such as halogen, hypohalous acid, halous acid, perhalic acid or salts thereof, or halogen oxide, nitrogen oxide or peroxide, as long as the oxidation reaction can be promoted. From the perspectives of availability and reactivity, sodium hypochlorite is preferred. The amount of the co-oxidant used is not particularly limited as long as the oxidation reaction can be promoted. Typically, the amount is approximately 1 mass % to 200 mass % relative to the solid content of the wood-based natural cellulose to be oxidized.

At least one compound selected from the group consisting of bromides and iodides may be used together with an N-oxyl compound and a co-oxidant. Thus, the oxidation reaction can progress smoothly, improving the efficiency of introducing a carboxyl group. As such a compound, sodium bromide or lithium bromide is preferred, and sodium bromide is more preferred from the perspectives of cost and stability. The amount of the compound used is not particularly limited as long as the oxidation reaction can be promoted. Typically, the amount is approximately 1 mass % to 50 mass % relative to the solid content of the wood-based natural cellulose to be oxidized.

The temperature of the oxidization reaction is preferred to be 4° C. to 80° C., and more preferred to be 10° C. to 70° C. If the reaction temperature is less than 4° C., reactivity of the reagents may lower and thus the reaction time may increase. If the reaction temperature is more than 80° C., side reactions may accelerate and thus the molecular weight of the sample may be lowered. This may lead to collapse of the rigid finely-disintegrated cellulose fiber structure having high crystallinity, preventing use as a stabilizer for an o/w emulsion.

The reaction time of the oxidation treatment may be appropriately determined considering reaction temperature, desired amount of a carboxyl group, and the like, but may typically be about 10 minutes to 5 hours, although it is not particularly limited thereto.

During oxidation reaction, pH of the reaction system is not particularly limited but is preferred to be in the range of 9 to 11. If pH is 9 or higher, reaction may efficiently proceed. If pH is higher than 11, side reactions may progress and decomposition of the sample may be accelerated. During the oxidation treatment, pH in the reaction system unavoidably lowers with the progress of oxidation due to generation of a carboxyl group. Therefore, pH of the reaction system is preferred to be maintained in the range of 9 to 11 during the oxidation treatment. The method of maintaining pH of the reaction system in the range of 9 to 11 may be a method in which an aqueous alkaline solution is added to the reaction system in response to lowering of pH.

The aqueous alkaline solution may be aqueous sodium hydroxide, aqueous lithium hydroxide, aqueous potassium hydroxide or aqueous ammonia solution, or an organic alkali, such as aqueous tetramethylammonium hydroxide solution, aqueous tetraethyl ammonium hydroxide solution, aqueous tetrabutylammonium hydroxide solution or aqueous benzyltrimethylammonium hydroxide solution, or other alkaline solutions. From the perspective of cost and the like, aqueous sodium hydroxide is preferred.

The oxidation reaction using an N-oxyl compound can be stopped by adding alcohol to the reaction system. In this case, pH of the reaction system is preferred to be maintained to the above range (pH 9 to 11). As the alcohol to be added, a low-molecular-weight alcohol, such as methanol, ethanol or propanol, is preferred because the reaction is quickly stopped. However, ethanol is especially preferred from the perspective of safety or the like of secondary products generated by the reaction.

The reaction solution resulting from the oxidation reaction may be directly used in the micronization process. However, the oxidized cellulose contained in the reaction solution is preferred to be collected and washed with a washing liquid to remove catalysts such as the N-oxyl compound, impurities, and the like. The oxidized cellulose may be collected by a known method, such as filtration, using a glass filter or a nylon mesh having a pore diameter of 20 μm. The washing liquid used for washing the oxidized cellulose is preferred to be pure water.

When the obtained TEMPO-oxidized cellulose is defibrated, cellulose single nanofibers (CSNF) can be obtained with a uniform fiber width of 3 nm. When CSNF is used as a raw material of the finely-disintegrated cellulose 11 for composite particles 15, droplets of the obtained o/w emulsion are likely to have a uniform size due to the uniform structure of CSNF.

As described above, CSNF used in the present embodiment can be obtained through a process of oxidizing raw cellulose materials, and a process of micronizing the cellulose materials and dispersing the finely-disintegrated cellulose into a liquid. The content of a carboxyl group introduced to CSNF is preferred to be in the range of 0.1 mmol/g or more and 5.0 mmol/g or less, and is more preferred to be 0.5 mmol/g or more and 2.0 mmol/g or less. If the content of the carboxyl group is less than 0.1 mmol/g, osmotic effects do not necessarily occur between the cellulose microfibrils, disabling entry of solvent. Therefore, it may be difficult to micronize cellulose for uniform dispersion. If the content of the carboxyl group exceeds 5.0 mmol/g, the molecular weight of the cellulose microfibrils may be lowered due to side reactions of the chemical treatment. Therefore, a rigid finely-disintegrated cellulose fiber structure having high crystallinity cannot be necessarily achieved, and thus the cellulose cannot be used as a stabilizer for an o/w emulsion.

(Step 2B)

In step 2B, surfaces of the polymerizable monomer droplets 12 are coated with the finely-disintegrated cellulose 11 in a dispersion liquid of finely-disintegrated cellulose, for stabilization as an emulsion.

Specifically, a polymerizable monomer is added to the dispersion liquid of finely-disintegrated cellulose obtained in step 1B and dispersed therein in the form of droplets. Furthermore, surfaces of the polymerizable monomer droplets 12 are coated with finely-disintegrated cellulose 11 to thereby prepare an o/w emulsion stabilized by the finely-disintegrated cellulose 11.

The method of preparing an o/w emulsion is not particularly limited but a typical emulsification method, e.g., various methods using homogenizers or machine stirring methods, may be used. Specifically, the method may be a mechanical treatment using a high-pressure homogenizer, ultrahigh-pressure homogenizer, multipurpose homogenizer, ball mill, roll mill, cutter mill, planetary mill, jet mill, attritor, grinder, blender, homomixer, ultrasonic homogenizer, nanogenizer, or underwater collision. A plurality of mechanical treatments may be combined.

In the case of using an ultrasonic homogenizer, for example, a polymerizable monomer may be added to the dispersion liquid of finely-disintegrated cellulose obtained in step 1B to obtain a mixed solvent. Then, the tip of the ultrasonic homogenizer may be inserted into the mixed solvent, for ultrasonic treatment. The conditions of treatment using an ultrasonic homogenizer are not particularly limited. However, for example, the frequency may be typically 20 kHz or more and the output may be typically 10 W/cm$^2$ or more. Duration of the treatment is not particularly limited but may typically be about 10 seconds to 1 hour.

Through the ultrasonic treatment, polymerizable monomer droplets 12 are dispersed in the dispersion liquid of finely-disintegrated cellulose to progress emulsification. Furthermore, the finely-disintegrated cellulose 11 is selectively adsorbed to the liquid/liquid interface between the monomer droplets 12 and the dispersion liquid of finely-disintegrated cellulose, so that the monomer droplets 12 are coated with the finely-disintegrated cellulose 11 and form a stabilized structure as an o/w emulsion. Thus, the emulsion stabilized with solids being adsorbed to the liquid/liquid interface is referred to as a Pickering emulsion. As mentioned above, the mechanism in which a Pickering emulsion is formed by finely-disintegrated cellulose fibers is not known. However, it is considered that, since cellulose has a hydrophilic site derived from a hydroxyl group and a hydrophobic site derived from a hydrocarbon group in the molecular structure thereof, i.e., has amphipathic nature, cellulose is adsorbed to the liquid/liquid interface between the hydrophobic monomer and the hydrophilic solvent, due to the amphipathic nature.

The o/w emulsion structure can be confirmed through optical microscope observation. Particle size in the o/w emulsion is not particularly limited but may typically be about 0.1 μm to 1,000 μm.

In the o/w emulsion structure, the thickness of the finely-disintegrated cellulose shell formed on each surface of the monomer droplet 12 is not particularly limited but may typically be about 3 nm to 1,000 nm. The thickness of the finely-disintegrated cellulose shell can be measured, for example, using a cryo-TEM.

Any type of polymerizable monomer may be used in step 2B as long as it is a monomer which has a structure including a polymerizable functional group, and which is in a liquid form at room temperature, is immiscible with water and can form a thermoplastic polymer (high-molecular-weight polymer) through a polymerization reaction. The polymerizable monomer that can be used in step 2B has only one polymerizable functional group. A polymerizable monomer having only one polymerizable functional group is referred to as a monofunctional monomer. It should be noted that a polymerizable monomer having two or more polymerizable functional groups is referred to as a polyfunctional monomer. The type of the monofunctional monomer is not particularly limited but may, for example, be a (meth)acrylic monomer, a vinyl monomer or the like. A polymerizable monomer having a cyclic ether structure such as an epoxy group or an oxetane structure (e.g., ε-caprolactone) may be used.

It should be noted that the term (meth)acrylate may refer to both acrylate and methacrylate.

Examples of monofunctional (meth)acrylic monomers include 2-hydroxyethyl (meth)acrylate, 2-hydroxypropyl (meth)acrylate, 2-hydroxybutyl (meth)acrylate, n-butyl (meth)acrylate, isobutyl (meth)acrylate, t-butyl (meth)acrylate, glycidyl (meth)acrylate, acryloylmorpholine, N-vinylpyrrolidone, tetrahydrofurfuryl acrylate, cyclohexyl (meth)acrylate, 2-ethylhexyl (meth)acrylate, isobornyl (meth)acrylate, isodecyl (meth)acrylate, lauryl (meth)acrylate, tridecyl (meth)acrylate, cetyl (meth)acrylate, stearyl (meth)acrylate, benzyl (meth)acrylate, 2-ethoxyethyl (meth) acrylate, 3-methoxybutyl (meth)acrylate, ethyl carbitol (meth)acrylate, phosphoric acid (meth)acrylate, ethylene oxide-modified phosphoric acid (meth)acrylate, phenoxy (meth)acrylate, ethylene oxide-modified phenoxy (meth) acrylate, propylene oxide-modified phenoxy (meth)acrylate, nonyl phenol (meth)acrylate, ethylene oxide-modified nonyl phenol (meth)acrylate, propylene oxide-modified nonyl phenol (meth)acrylate, methoxy diethylene glycol (meth)acrylate, methoxy polyethylene glycol (meth)acrylate, methoxy propylene glycol (meth)acrylate, 2-(meth)acryloyl oxyethyl-2-hydroxy propyl phthalate, 2-hydroxy-3-phenoxy propyl (meth)acrylate, 2-(meth)acryloyl oxyethyl hydrogen phthalate, 2-(meth)acryloyl oxypropyl hydrogen phthalate, 2-(meth)acryloyl oxypropyl hexahydro hydrogen phthalate, 2-(meth)acryloyl oxypropyl tetrahydro hydrogen phthalate, dimethylaminoethyl (meth)acrylate, trifluoroethyl (meth) acrylate, tetrafluoropropyl (meth)acrylate, hexafluoropropyl (meth)acrylate, octafluoropropyl (meth)acrylate, an adamantane derivative mono(meth)acrylate, such as adamantyl acrylate having a monovalent mono(meth)acrylate which is derived from 2-adamantane and adamantane diol, and other such monomers.

For example, the monofunctional vinyl monomer is preferred to be a vinyl ether-vinyl ester- or aromatic vinyl-based monomer or, in particular, is preferred to be styrene or a styrene-based monomer that is a liquid immiscible with water at room temperature.

The (meth)acrylate of the monofunctional vinyl monomer may be methyl (meth)acrylate, ethyl (meth)acrylate, butyl (meth)acrylate, t-butyl (meth)acrylate, 2-ethylhexyl (meth) acrylate, lauryl (meth)acrylate, alkyl (meth)acrylate, tridecyl (meth)acrylate, stearyl (meth)acrylate, cyclohexyl (meth) acrylate, benzyl (meth)acrylate, isobornyl (meth)acrylate, glycidyl (meth)acrylate, tetrahydrofurfuryl (meth)acrylate, an aryl (meth)acrylate, diethylaminoethyl (meth)acrylate, trifluoroethyl (meth)acrylate, heptafluorodecyl (meth)acrylate, dicyclopentenyl (meth)acrylate, dicyclopentenyloxyethyl (meth)acrylate, tricyclodecanyl (meth)acrylate, or the like.

Monofunctional aromatic vinyl monomers may be styrene, α-methyl styrene, o-methyl styrene, m-methyl styrene, p-methyl styrene, ethyl styrene, isopropenyl toluene, isobutyltoluene, tert-butyl styrene, vinyl naphthalene, vinyl biphenyl, 1,1-diphenylethylene, and the like.

In the present embodiment, besides these monomers, materials that can be used include, but are not limited to, polyether resin, polyester resin, polyurethane resin, epoxy resin, alkyd resin, spiroacetal resin, polybutadiene resin, polythiolpolyene resin and the like, which can be obtained by polymerizing a monomer having only one polymerizable functional group.

These polymerizable monomers may be used singly or in combination of two or more.

The weight ratio between the dispersion liquid of finely-disintegrated cellulose fibers and the polymerizable monomer that can be used in step 2B is not particularly limited. It is preferred, however, that the content of the polymerizable monomer is 1 part by mass or more to 50 parts by mass or less, relative to 100 parts by mass of the dispersion liquid of finely-disintegrated cellulose fibers. If the content of the polymerizable monomer is 1 part by mass or less, yield of the composite particles 15 may be lowered, which is not favorable. If the content exceeds 50 parts by mass, it may be difficult to uniformly coat the polymerizable monomer droplets 12 with the finely-disintegrated cellulose 11, which is not favorable.

The polymerizable monomer may contain a polymerization initiator in advance. Typically, a radical initiator, such as an organic peroxide or an azo polymerization initiator, is used as a polymerization initiator.

Examples of the organic peroxide include peroxyketals, hydroperoxides, dialkyl peroxides, diacyl peroxides, peroxycarbonates and peroxy esters.

The azo polymerization initiator may, for example, be ADVN, AIBN or the like.

Examples of the azo polymerization initiator include 2,2-azobis(isobutyronitrile) (AIBN), 2,2-Azobis(2-methylbutyronitrile) (AMBN), 2,2-azobis(2,4-dimethylvaleronitrile) (ADVN), 1,1-azobis(1-cyclohexanecarbonitrile) (ACHN), dimethyl-2,2-azobisisobutyrate (MAIB), 4,4-azobis(4-cyanovaleric acid) (ACVA), 1,1-azobis(1-acetoxy-1-phenylethane), 2,2-azobis(2-methylbutyramide), azobis(4-methoxy-2,4-dimethylvaleronitrile), 2,2-azobis(2-methylamidinopropane) dihydrochloride, 2,2-azobis[2-(2-imidazolin-2-yl) propane], 2,2-azobis[2-methyl-N-(2-hydroxyethyl) propionamide], 2,2-azobis(2,4,4-trimethylpentane), 2-cyano-2-propylazoformamide, 2,2-azobis(N-butyl-2-methylpropionamide) and 2,2-azobis(N-cyclohexyl-2-methylpropionamide).

If a polymerizable monomer comprising a polymerization initiator in advance is used in step 2B, the polymerizable monomer droplets 12 in the emulsion particles after formation of an o/w emulsion will comprise the polymerization initiator. Thus, when polymerizing the monomer in the emulsion in step 3B described later, polymerization reaction may more easily progress.

The weight ratio between the polymerizable monomer that can be used in step 2B and a polymerization initiator is not particularly limited. It is preferred, however, that the content of the polymerization initiator is 0.1 parts by mass or more relative to 100 parts by mass of polymerizable monomer. If the content of the polymerizable initiator is less than 0.1 parts by mass, polymerization reaction does not necessarily sufficiently progress, and yield of the composite particles 15 lowers, which is unfavorable.

The polymerizable monomer may additionally contain in advance another functional component besides the polymerization initiator. Specifically, such an additional functional component may be, a magnetic material, pharmaceutical, pesticide, fragrance, adhesive, enzyme, pigment, dye, deodorant, metal, metal oxide, inorganic oxide or the like. If the polymerizable monomer additionally contains in advance another functional component besides a polymerization initiator, particles formed as composite particles 15 are permitted to contain this functional component therein so as to exhibit a function suitable for the usage.

(Step 3B)

In step 3B, pH of the emulsion is controlled to 3.5 or less.

The method of controlling pH to 3.5 or less is not particularly limited. For example, a method of appropriately adding an acid may be used. The acid used is not particularly limited but hydrochloric acid is preferred from the perspective of availability or safety.

When the pH is less than 3.5, the aqueous CNF dispersion corresponding to the continuous phase of the emulsion may aggregate and form a gel, so that a gel comprising emulsion droplets can be obtained. In this case, pH of the emulsion is not particularly limited as long as it is 3.5 or less. However, if the pH is less than 2, CNF may tend to deteriorate due to acid hydrolysis during polymerization reaction in the subsequent step 4B. Therefore, pH of the emulsion is preferred to be controlled in the range of 2 or more and 3.5 or less.

(Step 4B)

In step 4A, the polymerizable monomer droplets 12 contained in the CNF gel obtained in step 3B are polymerized to obtain composite particles 15 in which polymer particles 13 are coated with finely-disintegrated cellulose 11.

The method of polymerizing a polymerizable monomer is not particularly limited, but may be appropriately selected according to the type of the polymerizable monomer used and the type of the polymerization initiator used. For example, the method may be suspension polymerization.

The specific method of suspension polymerization is not particularly limited but may be a known method. For example, the o/w emulsion, prepared in step 3B, stabilized by coating the monomer droplets 12 comprising a polymerization initiator with the finely-disintegrated cellulose 11 and by allowing the aqueous finely-disintegrated cellulose 11 dispersion phase to form a gel, may be heated while being stirred, for suspension polymerization. The method of stirring is not particularly limited but a known method may be used. Specifically, a disperser or a stirrer may be used. The o/w emulsion may only be heated without being stirred. The heating temperature may be appropriately determined according to the type of the polymerizable monomer and the type of the polymerization initiator, but is preferred to be in the range of 20° C. or more and 150° C. or less. If the heating temperature is less than 20° C., the reaction rate of polymerization may be lowered, which is unfavorable. If the heating temperature exceeds 150° C., the finely-disintegrated cellulose 11 may be modified, which is unfavorable. Polymerization reaction time may be appropriately determined according to the type of the polymerizable monomer and the type of the polymerization initiator, but may typically be about 1 hour to 24 hours. Polymerization reaction may be induced by irradiating the o/w emulsion with ultraviolet light which is a type of electromagnetic wave. Besides electromagnetic wave, a particle beam, such as an electron beam, may be used.

Through the above processing, composite particles 15 can be prepared, in which polymer particles 13 are coated with finely-disintegrated cellulose 11. In this processing, the polymerization reaction progresses in a state of the aqueous finely-disintegrated cellulose 11 dispersion phase as a continuous phase of the emulsion aggregating and forming a gel. Therefore, the monomer droplets 12 are more easily maintained in shape, so that composite particles can be efficiently obtained.

Even when polymerization reaction progresses in a state of the aqueous CNF dispersion phase as a continuous phase of the emulsion aggregating and forming a gel, the finely-disintegrated cellulose 11 adsorbed to the liquid/liquid interfaces of the monomer droplets 12 is retained. This is considered to be because the amphipathic finely-disintegrated cellulose 11 is more easily adsorbed to the liquid/liquid interfaces due to the aqueous CNF dispersion liquid phase forming a gel.

Immediately after completion of polymerization reaction in step 4B, the dispersion liquid of the composite particles 15 is in a state in which a large quantity of water is mixed with liberated finely-disintegrated cellulose 11 that has not contributed to formation of coatings for the composite particles 15. Therefore, the prepared composite particles 15 are required to be collected and purified. The method of collection and purification is preferred to be centrifugal washing or filtration washing. If the aqueous CNF dispersion phase remains in the state of a gel, collection and purification of the composite particles 15 may be difficult. Therefore, an aqueous alkaline solution is preferred to be added to the composition immediately after completion of polymerization reaction to control pH to an alkaline side (more preferred to be controlled to pH 10 or more) and restore fluidity of the aqueous CNF dispersion phase. The aqueous alkaline solution to be used is not particularly limited but may, for example, be aqueous sodium hydroxide. The pH level is not particularly limited but may be controlled to any level as long as fluidity of the aqueous CNF dispersion phase can be restored. However, if the pH is 13 or more, CNF may more easily deteriorate. Accordingly, the pH is preferred to be controlled to less than 13. The centrifugal washing may be a known method. Specifically, the composite particles 15 may be settled by centrifugation for removal of the supernatant, followed by redispersion in a water-methanol mixed solvent. After repeating these processes, residual solvent may be removed from the sediment obtained by final centrifugation to thereby collect composite particles 15. The filtration washing may also be a known method. For example, the prepared composite particles 15 may be repeatedly subjected to suction filtration using a PTFE membrane filter having a pore size of 0.1 μm. After that, residual solvent may further be removed from the paste finally remaining on the membrane filter to thereby collect the composite particles 15.

The method of removing residual solvent is not particularly limited but may be air drying or thermal drying in an oven. The dry solids comprising the composite particles 15 obtained in this way do not form a film or aggregate but are in the form of a fine-textured powder.

<Molding Resin Composition>

The composite particles 15 obtained in the present embodiment are composite particles of cellulose nanofibers and a thermoplastic resin. Accordingly, by further kneading the composite particles 15 with a thermoplastic resin, a molding resin composition (also termed master batch) can be obtained. The composite particles 15 alone may be used as a master batch. Various types of resin molding can be more easily obtained by using the master batch. The method of producing resin molding is not particularly limited. For example, a known method, such as injection molding, blow molding, compression molding or foam molding, may be used. The obtained resin molding, in which cellulose nanofibers are well dispersed, can be used as resin molding improved in strength properties or thermal dimensional stability.

(Resin Molding)

Resin molding may be formed of the composite particles 15 alone obtained in the present embodiment. The obtained resin molding will have high content of cellulose nanofibers and accordingly strength properties or thermal dimensional stability may be improved even more. For example, the obtained resin molding may be used for a 3D printer modeling material or the like. Utilizing the characteristics of cellulose nanofibers, the composite particles 15 may be used for a resin molding material which is applied to usages requiring transparency and high strength properties.

Advantageous Effects of Fourth Embodiment

The composite particles 15 of the present embodiment are new composite particles comprising a thermoplastic resin and CNF, which can be dehydrated with a simple and more easy method and can more easily form a composite with a resin.

In the composite particles 15 of the present embodiment, a thermoplastic resin and CNF form a composite in micro-size order. Therefore, these thermoplastic resin and CNF can be kneaded together in a short residence time and can more easily form a composite. When the CNF/thermoplastic resin composite is extruded and molded, the obtained molding is expected to exert stable strength properties.

According to the present embodiment, there is provided a method of producing new composite particles 15 and dry solids of the composite particles 15. This method imposes only low environmental load and can more easily provide the composite particles 15.

The fourth embodiment of the present invention has been specifically described referring to the drawings. However, specific configurations of the present invention should not be limited to this embodiment but the present invention should include design changes and the like within the scope not departing from the spirit of the present invention. The components shown in the fourth embodiment and the modifications may be appropriately combined.

Fifth Embodiment

Next, a fifth embodiment of the present invention will be described based on the second aspect of the production method. Composite particles 15 obtained in the present embodiment are configured as in the fourth embodiment. However, the present embodiment is different from the fourth embodiment in that, in step 3C of the production method, the emulsion system is deoxygenated instead of controlling pH of the emulsion. In the following description, like reference signs designate common parts already described to omit duplicate description.

<Method of Producing Composite Particles>

Next, a method of producing composite particles 15 according to the present embodiment will be described.

The method of producing composite particles 15 of the present embodiment include a step of defibrating raw cellulose materials in a solvent to obtain a dispersion liquid of finely-disintegrated cellulose (step 1B); a step of coating surfaces of polymerizable monomer droplets 12 with finely-disintegrated cellulose 11 in the dispersion liquid of finely-disintegrated cellulose to achieve stability as an emulsion (step 2B); a step of deoxygenating the polymerizable monomer droplets in the emulsion (emulsion system) (step 3C); and a step of polymerizing the polymerizable monomer droplets, while maintaining the state of the system being deoxygenated, to obtain composite particles 15 in which polymer particles 13 are coated with the finely-disintegrated cellulose 11 (step 4C).

Each step will be specifically described below.

(Steps 1B and 2B)

Steps 1B and 2B are the same as those of the fourth embodiment.

(Step 3C)

Step 3C is a deoxygenation step in which oxygen in the emulsion system obtained in step 2B is removed. The method of deoxygenation is not particularly limited but a known method may be appropriately used. For example, an inert gas, such as nitrogen gas or argon gas, may be blown into the emulsion system to make it inert. After completion of deoxygenation, the reaction container may be immediately hermetically closed to maintain the deoxygenated state, followed by step 4C. Alternatively, step 4C may be performed while an inert gas is continuously supplied.

(Step 4C)

Step 4C is basically the same as step 4B of the fourth embodiment. In the fifth embodiment, the initiator or the growing polymer radicals will not be deactivated during polymerization of the monomer by reaction with oxygen, because the emulsion system has been deoxygenated in step 3C. Accordingly, the polymerization reaction uniformly progresses with ease, with the shape of the monomer droplets 12 being maintained, so that composite particles can be efficiently obtained.

Through the processing described above, a dispersion liquid of composite particles 15 can also be obtained in the present embodiment. The method of collecting the composite particles may be centrifugal or filtration washing which is basically the same as in the fourth embodiment.

Advantageous Effects of Fifth Embodiment

According to the composite particles 15 of the present embodiment, advantageous effects similar to those of the fourth embodiment can be obtained.

It should be noted that the pH control in step 3B of the fourth embodiment may be combined with the deoxygenation in step 3C of the fifth embodiment. Specifically, while an inert gas, such as nitrogen gas or argon gas, is introduced into the emulsion, pH of the emulsion may be controlled to 3.5 or lower so that the aqueous CNF dispersion phase may form a gel, and in this state, step 4C may be performed.

The fifth embodiment of the present invention has been specifically described referring to the drawings. However, specific configurations of the present invention should not be limited to this embodiment but the present invention should include design changes and the like within the scope not departing from the spirit of the present invention. The components shown in the fifth embodiment and the modifications may be appropriately combined.

EXAMPLES

Hereinafter, the present invention will be described in detail based on examples. However, the technical scope of the present invention should not be limited to these examples. In the following examples, the sign % refers to mass % (w/w %) unless otherwise noted.

Example 1

(Step 1A: Step of Obtaining Cellulose Nanofiber Dispersion Liquid) (TEMPO Oxidization of Wood Cellulose)

70 g of softwood kraft pulp was suspended in 3,500 g of distilled water, to which a solution obtained by dissolving 0.7 g of TEMPO and 7 g of sodium bromide into 350 g of distilled water was added, followed by cooling to 20° C. To this, 450 g of aqueous sodium hypochlorite solution at 2 mol/L and 1.15 g/mL density was dripped to start an oxidation reaction. The temperature in the system was constantly maintained at 20° C. During the reaction, 0.5 N aqueous sodium hydroxide was added in response to the lowering of pH. When the sum of addition of the sodium hydroxide reached 3.50 mmol/g relative to the weight of the cellulose, approximately 100 mL of ethanol was added to stop the reaction. After that, filtration washing was repeatedly performed using a glass filter and distilled water to obtain an oxidized pulp.

(Measurement of Carboxyl Group of Oxidized Pulp)

0.1 g of solids of the oxidized pulp and reoxidized pulp obtained through the TEMPO oxidation were dispersed in water at 1% concentration, followed by adding hydrochloric acid to control pH to 2.5. Then, the amount of the carboxyl group (mmol/g) was calculated based on conductometric titration using 0.5 M aqueous sodium hydroxide. The result was 1.6 mmol/g.

(Defibration of Oxidized Pulp)

Figure 2:
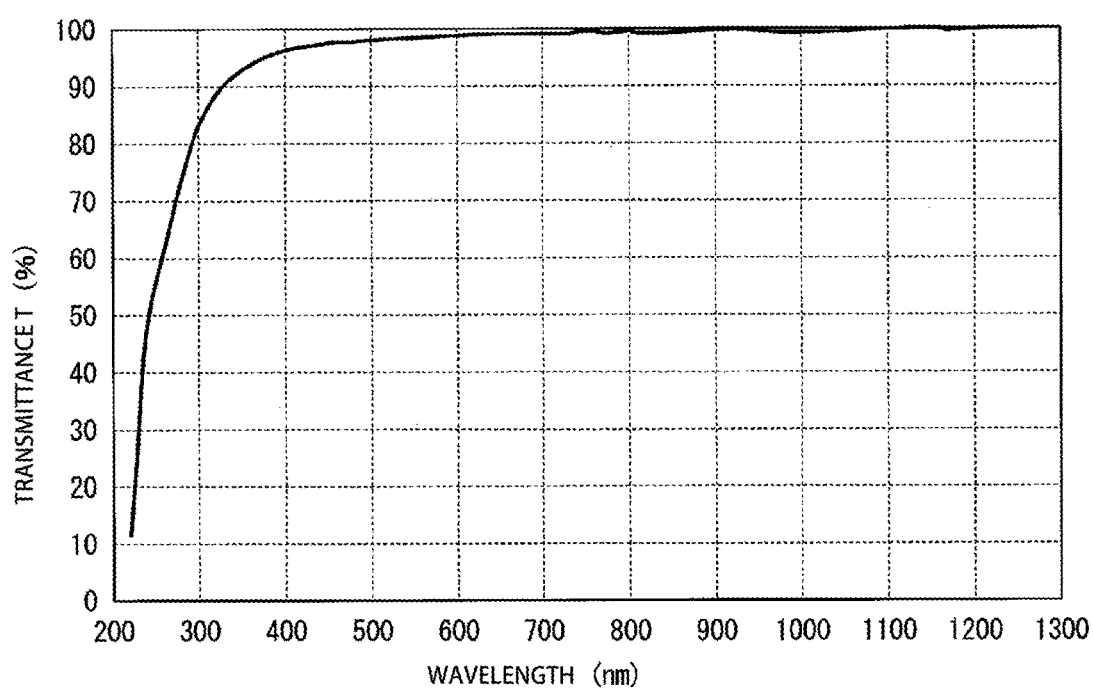
FIG. 2 is a diagram illustrating measurements of transmission spectrum of an aqueous dispersion liquid of finely-disintegrated cellulose obtained in Example 1.
Figure 3:
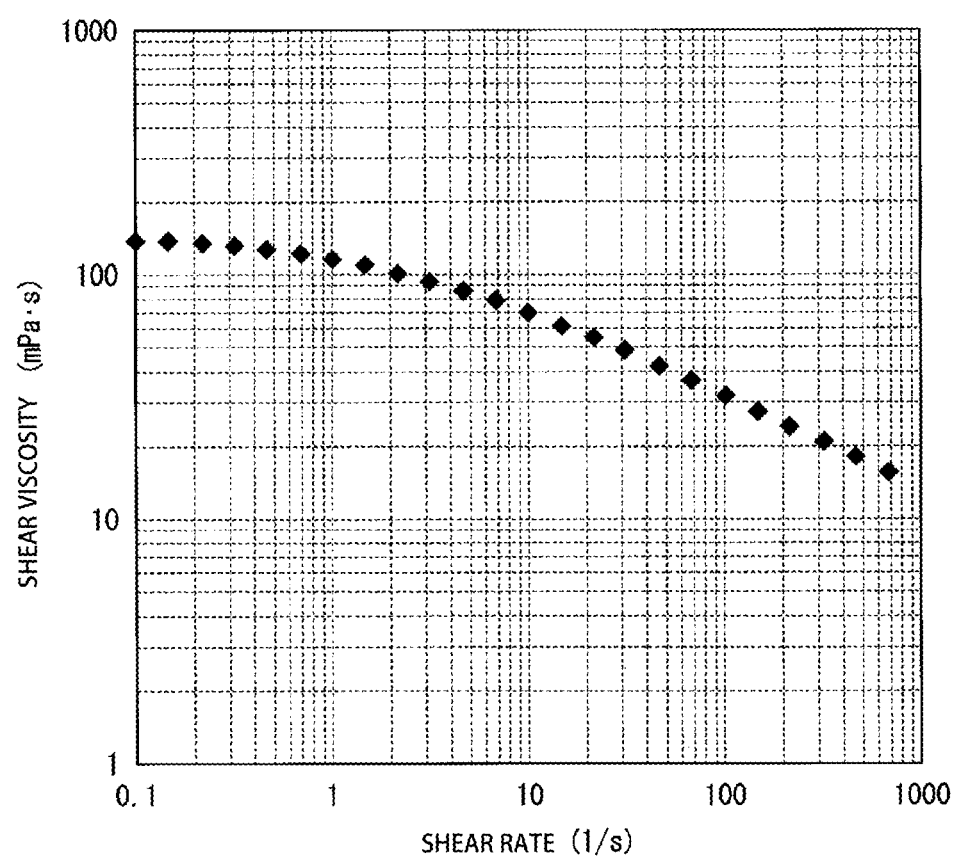
FIG. 3 is a diagram illustrating measurements of static viscoelasticity measured by a rheometer for an aqueous dispersion liquid of finely-disintegrated cellulose obtained in Example 1.

1 g of the oxidized pulp obtained through the TEMPO oxidation was dispersed in 99 g of distilled water and micronized for 30 minutes by means of a blender to obtain an aqueous CSNF dispersion liquid at a CSNF concentration of 1%. The CSNF dispersion liquid was put into a quartz cell having a light path length of 1 cm to measure transmission spectrum by using a spectrophotometer (UV-3600 manufactured by Shimadzu Corporation). The results are shown in FIG. 2. As is apparent from FIG. 2, the aqueous CSNF dispersion liquid showed high transparency. The number average minor axis diameter of CSNF contained in the aqueous CSNF dispersion liquid was 3 nm, and the number average major axis diameter thereof was 1,110 nm. Furthermore, static viscoelasticity was measured by using a rheometer. The results are shown in FIG. 3. As is apparent from FIG. 3, the CSNF dispersion liquid exhibited thixotropic properties.

(Step 2A: Step of Preparing o/w Emulsion)

Next, 1 g of 2,2-azobis-2,4-dimethylvaleronitrile (also termed ADVN hereinafter) as a polymerization initiator was dissolved into 10 g of divinylbenzene (also termed DVB hereinafter) as a polymerizable monomer. When all the DVB/ADVN mixed solution was added to 40 g of 1% CSNF concentration dispersion liquid, the DVB/ADVN mixed solution and the CSNF dispersion liquid were separated into two layers both with high transparency.

Next, a shaft of an ultrasonic homogenizer was inserted into the mixed liquid that had been separated into two layers, from above the liquid surface of the upper layer, and ultrasonic homogenization was performed for 3 minutes at a frequency of 24 kHz and output of 400 W. After being ultrasonically homogenized, the mixed liquid appeared to be a cloudy emulsion. A droplet of the mixed liquid was dropped onto a glass slide, sealed with a glass cover and observed through an optical microscope. Through the observation, it was confirmed that innumerable emulsion droplets of about 1 μm to several micrometers in size were produced and the droplets were dispersed and stabilized as an o/w emulsion.

(Step 3A: Step of Obtaining Composite Particles 5 Coated with CNF Through Polymerization Reaction)

The dispersion liquid of the o/w emulsion was water-bathed at a temperature of 70° C. for 8 hours while being stirred by a stirrer to undergo polymerization reaction. After 8 hours, the dispersion liquid was cooled to room temperature. The dispersion liquid appeared to remain unchanged before and after the polymerization reaction. The obtained dispersion liquid was centrifuged at a centrifugal force of 75,000 g (g indicates gravitational acceleration) for 5 minutes to obtain a sediment. The supernatant was removed by decantation to collect the sediment which was then repeatedly washed using pure water and methanol using a PTFE membrane filter having a pore size of 0.1 μm. The purified and collected substances obtained were redispersed in a solvent at 1% concentration to evaluate the particle size by using a particle size analyzer (NANOTRAC UPA-EX150 manufactured by Nikkiso Co., Ltd.). The average particle size was 2.1 μm. Then, the purified and collected substances were air-dried, followed by vacuum drying at a temperature of 25° C. for 24 hours. As a result, a fine-textured dry powder (composite particles 5) was obtained.

(Shape Observation Through Scanning Electron Microscope)

Figure 4:
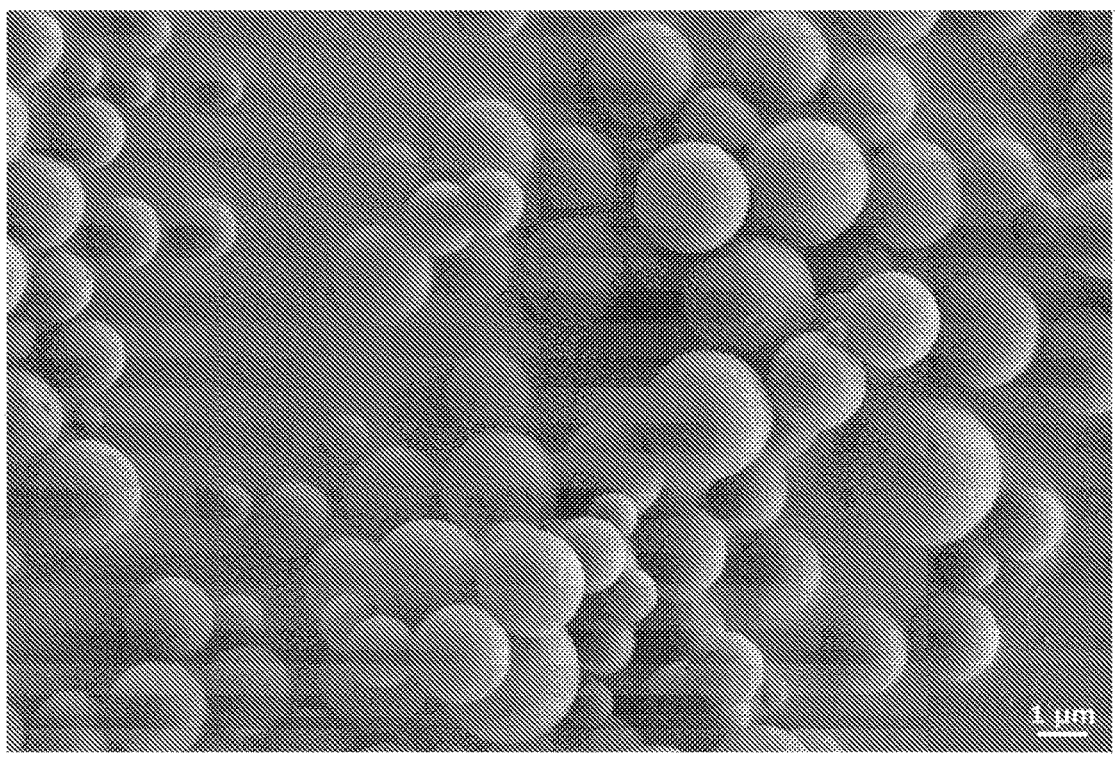
FIG. 4 is a scanning electron microscope (SEM) image of composite particles obtained in Example 1.
Figure 5:
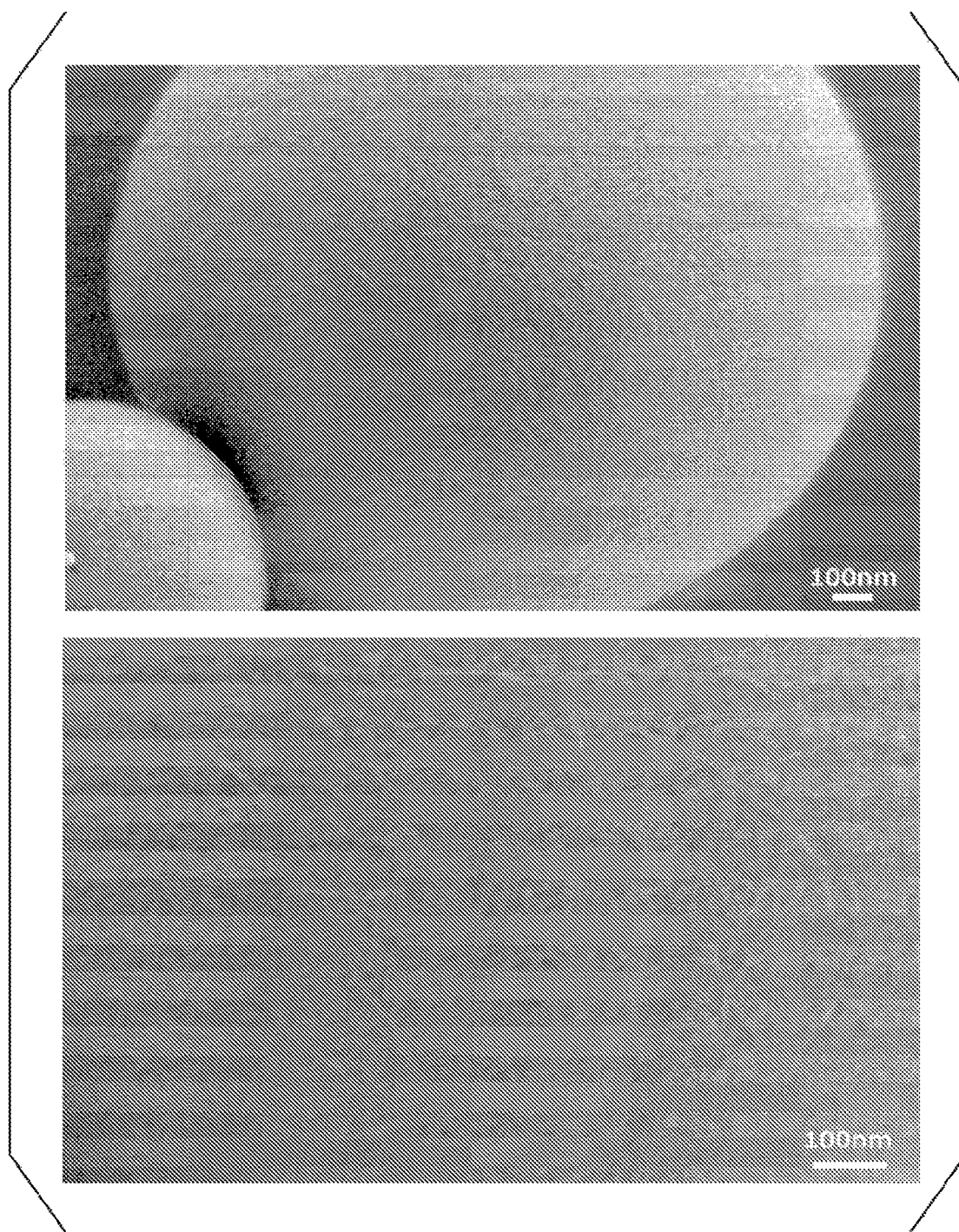
FIG. 5 is a set of highly magnified scanning electron microscope (SEM) images of composite particles obtained in Example 1.

The obtained dry powder was observed through a scanning electron microscope. The results are shown in FIGS. 4 and 5. As is apparent from FIG. 4, it was confirmed that innumerable perfectly spherical composite particles 5 were formed, which were derived from the shape of the emulsion droplets, as a result of the polymerization reaction using the o/w emulsion droplets as a template. Furthermore, as shown in FIG. 5, it was confirmed that the surfaces of the composite particles 5 were uniformly coated with CNF having a width of several nanometers. In spite of being repeatedly washed by filtration washing, surfaces of the composite particles 5 were uniformly coated with CNF1, which meant that the polymer inside the composite particles and CNF were bonded together and were in an inseparable state.

(Evaluation of Redispersibility)

A dry powder of composite particles 5 was added to pure water at 1% concentration and redispersed by a stirrer. The dry powder more easily dispersed and formed no aggregate. Furthermore, particle size was evaluated by using a particle size analyzer. The average particle size was 2.1 μm as before drying. The data resulting from the particle size analyzer showed no sign of aggregation. As set forth above, in spite of the surfaces of the composite particles 5 being covered with CNF, the composite particles 5 were not formed into a film due to drying but were obtained in the form of a powder, and also exhibited good redispersibility.

(Step 4A: Step of Providing New Component to CNF1 on the Surfaces of Composite Particles 5)

A dry powder of composite particles 5 was added to pure water at 1% concentration and redispersed by a stirrer. This composite particle dispersion liquid was experimented on as follows.

(Preparation of Aqueous Chloroauric Acid Solution)

2.47 M aqueous chloroauric acid solution was purchased from Tanaka Kikinzoku Kogyo and diluted with water to prepare 10 mM aqueous chloroauric acid solution (Preparation of Aqueous Sodium Borohydride)

Sodium borohydride was dissolved in distilled water to prepare 20 mM aqueous sodium borohydride.

(Step of Compounding Gold Nanoparticles with CNF1 on Surfaces of Composite Particles 5)

0.5 g of 10 mM aqueous chloroauric acid solution was added to 10 g of 1% concentration composite particle dispersion liquid, while the liquid was stirred by a stirrer with a constant temperature (25° C.) being maintained. After 30-minute stirring, 1 g of 20 mM aqueous sodium borohydride was added to the dispersion liquid. Then, stirring was continued another 30 minutes to thereby prepare a dispersion liquid comprising gold nanoparticle-carrying composite particles 5B. The obtained dispersion liquid exhibited a vivid pink color derived from gold nano particles, showing the formation of gold nanoparticles As in step 3A, the metal-carrying composite particles 5B contained in the obtained dispersion liquid were collected and purified by centrifugal washing and filtration washing, followed by drying. As a result, a vivid pink fine-textured dry powder was obtained.

(Evaluation of Redispersibility)

Redispersibility was also evaluated as in step 3A. The obtained vivid pink fine-textured dry powder had very good redispersibility. As in step 3A, particle size distribution before and after drying was compared by using a particle size analyzer. The average particle size was 2.1 μm both before and after drying. The color before and after drying remained unchanged, and a vivid pink color derived from gold nanoparticles was presented.

(Shape Observation Through Scanning Electron Microscope)

Figure 6:
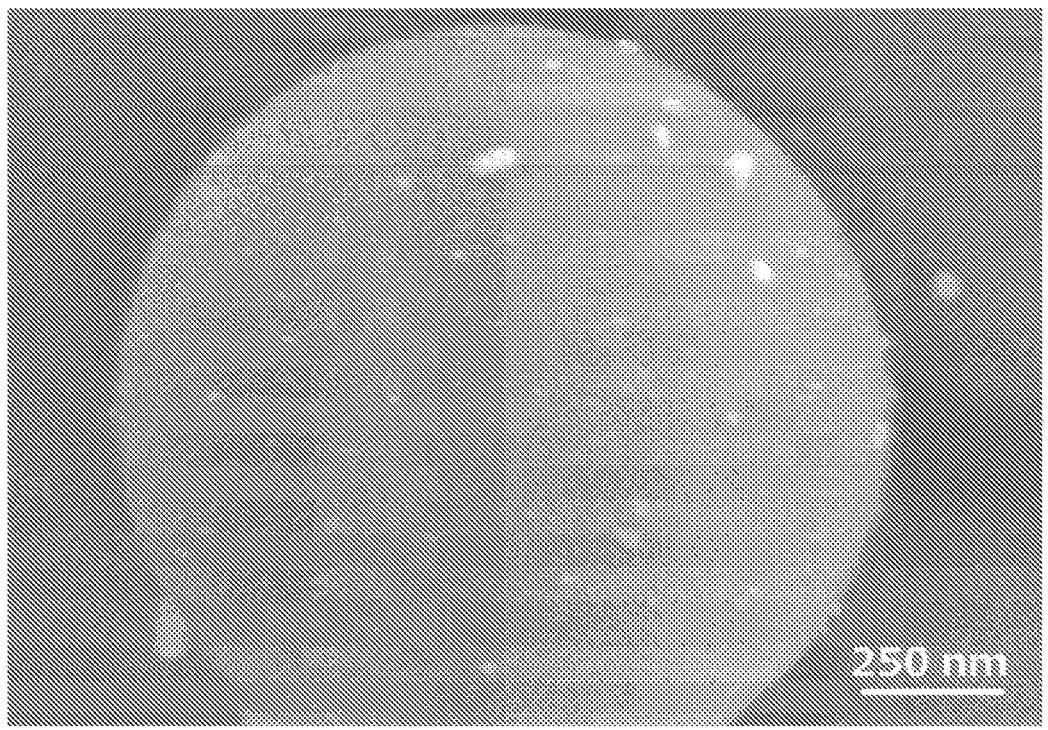
FIG. 6 is a highly magnified scanning electron microscope (SEM) image of a gold nanoparticle-carrying CNF/polymer composite particle obtained in Example 1.

The obtained dry powder was observed through a scanning electron microscope. The results are shown in FIG. 6. As is apparent from FIG. 6, it was confirmed that gold nanoparticles were precipitated on the surfaces of the composite particles 5B and thus the composite particles 5B formed a composite with gold nanoparticles. In spite of the composite particles 5B being repeatedly washed by filtration washing, gold nanoparticles were supported on the surfaces of the composite particles 5B, and the obtained dry powder of the metal-carrying composite particles 5B exhibited a vivid pink color. This meant that, in the metal-carrying composite particles 5B of the present embodiment, CNF1 on the surfaces of the composite particles 5B and gold nanoparticles were bonded together and were in an inseparable state.

As set forth above, the present example showed that composite particles could be provided as a usable dry powder which could be redispersed, with the gold nanoparticles forming no aggregate, and which caused no change in wavelength of localized surface plasmon resonance before and after drying.

Example 2

Composite particles 5B were prepared under the same conditions as in Example 1 except that diethylene glycol diacrylate (product name: FA-222A manufactured by Hitachi Chemical Company, Ltd., also termed FA-222A hereinafter) was used instead of DVB. The composite particles 5B were evaluated as in Example 1.

Example 3

Composite particles were prepared under the same conditions as in Example 1 except that hexanediol diacrylate (product name: A-HD-N manufactured by Shin-Nakamura Chemical Co., Ltd., also termed A-HD-N hereinafter) was used instead of DVB. The composite particles were evaluated as in Example 1.

Example 4

Composite particles 5B were prepared under the same conditions as in Example 1 except that 2,2-azobis-isobutyronitrile (also termed AIBN hereinafter) was used instead of ADVN. The composite particles 5B were evaluated as in Example 1.

Example 5

Composite particles 5B were prepared under the same conditions as in Example 1 except that a carboxymethylated (also termed C-methylated hereinafter) CNF dispersion liquid was used. This C-methylated CNF dispersion liquid was obtained according to the carboxymethylation, instead of TEMPO oxidization, disclosed in Patent Document 2. The composite particles 5B were evaluated as in Example 1.

Example 6

Composite particles 5B were prepared under the same conditions as in Example 1 except that a phosphate esterified CNF dispersion liquid was used. This phosphate esterified CNF dispersion liquid was obtained according to the phosphate esterification, instead of TEMPO oxidization, disclosed in Non-Patent Document 1. The composite particles 5B were evaluated as in Example 1.

Example 7

Composite particles 5B were prepared under the same conditions as in Example 1 except that silver nitrate was used instead of chloroauric acid. The composite particles 5B were evaluated as in Example 1. The obtained composite particle dispersion liquid and dry powder of the composite particles exhibited a vivid yellow color.

Example 8

Composite particles 5C were prepared under the same conditions as in Example 1 except that the processing included auxiliary step 1A and did not include step 4A. The composite particles 5C were evaluated as in Example 1. Specifically, according to the method disclosed in Patent Document 5, gold nanoparticles were precipitated, as auxiliary step 1A, on the CSNF surfaces in the obtained aqueous CSNF dispersion liquid. The obtained gold nanoparticle-carrying CSNF dispersion liquid exhibited a vivid red color. The gold nanoparticle-carrying CSNF dispersion liquid was appropriately evaporated to control the concentration to about 1% and then step 2A and the subsequent steps were performed. Finally, a dry powder exhibiting a vivid pink color was obtained as in Example 1.

Comparative Example 1

Composite particles were prepared under the same conditions as in Example 1 except that pure water was used instead of the CSNF dispersion liquid.

Comparative Example 2

Composite particles were prepared under the same conditions as in Example 1 except that carboxymethyl cellulose (also termed CMC hereinafter) was used instead of the CSNF dispersion liquid.

Comparative Example 3

Composite particles were prepared by performing step 4A as in Example 1 by using a dispersion liquid in which styrene-divinylbenzene copolymer microbeads (having a particle size of 4.5 μm manufactured by Techno Chemical Corporation) were dispersed instead of the composite particles of the present invention.

The examples and comparative examples set forth above were evaluated as shown in the following Table 1.

TABLE 1

| | Stabilizer for emulsion | Monomer | Polymerization initiator | Result of step 2A | Result of step 3A | Metal used for step 4A | Result of step 4A | Redispersibility |
|---|---|---|---|---|---|---|---|---|
| Example 1 | TEMPO oxidized CNF | DVB | ADVN | A | A | Gold | A | A |
| Example 2 | TEMPO oxidized CNF | FA-222A | ADVN | A | A | Gold | A | A |
| Example 3 | TEMPO oxidized CNF | A-HD-N | ADVN | A | A | Gold | A | A |
| Example 4 | TEMPO oxidized CNF | DVB | AIBN | A | A | Gold | A | A |
| Example 5 | C-methylated CNF | DVB | ADVN | A | A | Gold | A | A |
| Example 6 | Phosphate esterified CNF | DVB | ADVN | A | A | Gold | A | A |
| Example 7 | TEMPO oxidized CNF | DVB | ADVN | A | A | Silver | A | A |
| Example 8 | TEMPO oxidized CNF | DVB | ADVN | A | A | | | A |
| Comparative Example 1 | None (only pure water) | DVB | ADVN | B | | | | |
| Comparative Example 2 | CMC | DVB | ADVN | A | B | | | |
| Comparative Example 3 | Commercially available microbeads | | | | | Gold | B | |

In table 1, the "stabilizer for the emulsion" refers to an additive used for stabilizing the o/w emulsion in step 2A and corresponds, for example, to the finely-disintegrated cellulose 1 of the above embodiments.

The result of step 2A was evaluated as A when an o/w emulsion could be formed, and B when no o/w emulsion could be formed.

The result of step 3A was evaluated as A when perfectly spherical particles were obtained using the emulsion of step 3A as a template, and B when such particles were not obtained.

The result of step 4A was evaluated as A when metal nanoparticles could be supported on the surfaces of the particles, and B when metal nano particles could not be supported on the surfaces of the particles.

Redispersibility was evaluated as A when there was no change in redispersibility of particles carrying metal nanoparticles and in wavelength of plasmon resonance derived from the metal nanoparticles before and after drying, and B when there was a change in redispersibility of particles carrying metal nanoparticles and in wavelength of plasmon resonance derived from the metal nanoparticles before and after drying.

In Table 1, the diagonal lines in the cells of comparative examples indicate that performing the step was impossible and no subsequent steps were performed.

As is apparent from the evaluations of Examples 1 to 8 in Table 1, it was confirmed that metal-carrying composite particles 5B could be prepared irrespective of the types of finely-disintegrated cellulose 1 (TEMPO oxidized CNF, C-methylated CNF or phosphate esterified CNF) or the types of monomer or the types of initiator, and that these examples contributed to solving the issues of the present invention.

In Comparative Example 1, performing step 2A was impossible. Specifically, in spite of the ultrasonic homogenization treatment being performed, the monomer layer and the CNF dispersion liquid layer remained as two separate layers, disabling preparation of an o/w emulsion.

In Comparative Example 2, an o/w emulsion could be formed in step 2A. This is considered to be because CMC showed amphipathic nature as finely-disintegrated cellulose did, and functioned as a stabilizer for the emulsion. However, when undergoing polymerization reaction in the subsequent step 3A, the emulsion was destabilized and thus no composite particles could be obtained using the o/w emulsion as a template. The reason for this destabilization of the emulsion during polymerization reaction is not known but is considered to be because CMC, which was miscible with water, was too fragile as coatings to maintain the emulsion during the polymerization reaction.

In Comparative Example 3, commercially available microbeads were used, which were configured similarly to the composite particles of the present invention but were not coated with CNF. Carrying of gold nanoparticles was attempted, however, no color derived from LSPR of gold nanoparticles was observed but only a black or brown dispersion liquid remained. In the subsequent filtration washing, color was completely removed. SEM shape observation was performed but no microbeads were confirmed to carry gold nanoparticles.

Example 9

(Step 1B: Step of Obtaining Cellulose Nanofiber Dispersion Liquid) (TEMPO Oxidization of Wood Cellulose)

70 g of softwood kraft pulp was suspended in 3,500 g of distilled water, to which a solution obtained by dissolving 0.7 g of TEMPO and 7 g of sodium bromide into 350 g of distilled water was added, followed by cooling to 20° C. To this, 450 g of aqueous sodium hypochlorite solution at 2 mol/L and 1.15 g/mL density was dripped to start an oxidation reaction. The temperature in the system was constantly maintained at 20° C. During the reaction, 0.5 N aqueous sodium hydroxide was added in response to the lowering of pH. When the sum of addition of the sodium hydroxide reached 3.50 mmol/g relative to the weight of the cellulose, approximately 100 mL of ethanol was added to stop the reaction. After that, filtration washing was repeatedly performed using a glass filter and distilled water to obtain an oxidized pulp.

(Measurement of Carboxyl Group of Oxidized Pulp)

0.1 g of solids of the oxidized pulp and reoxidized pulp obtained through the TEMPO oxidation were dispersed in water at 1% concentration, followed by adding hydrochloric acid to control pH to 2.5. Then, the amount of the carboxyl group (mmol/g) was calculated based on conductometric titration using 0.5 M aqueous sodium hydroxide. The result was 1.6 mmol/g.

(Defibration of Oxidized Pulp)

Figure 8:
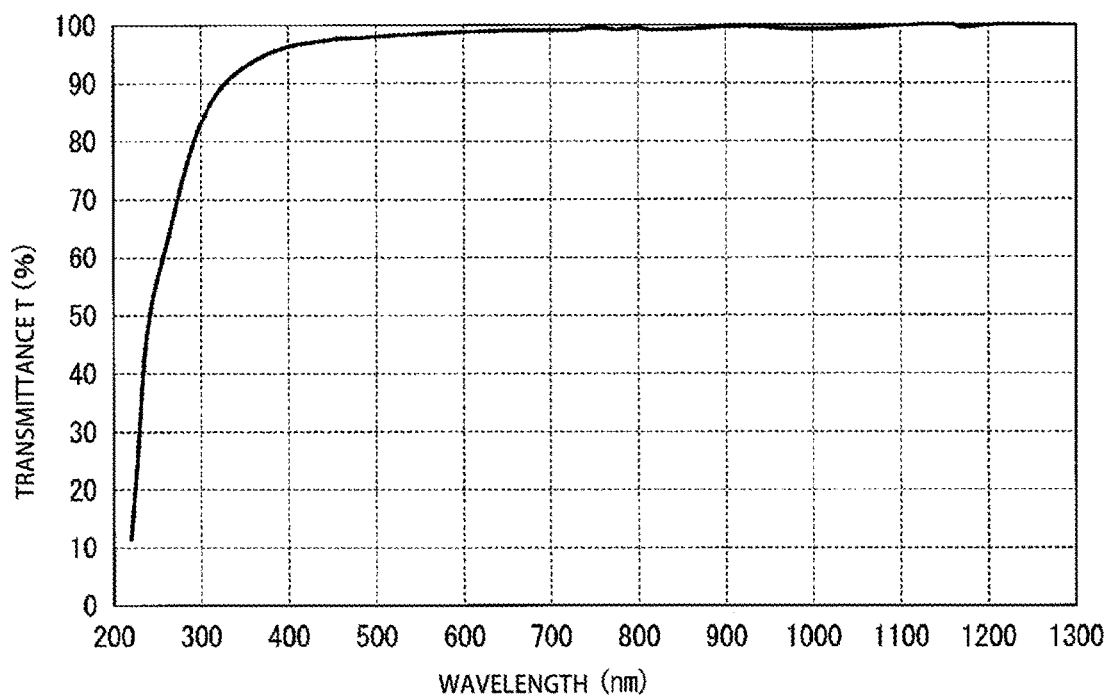
FIG. 8 is a diagram illustrating measurements of transmission spectrum of an aqueous dispersion liquid of finely-disintegrated cellulose obtained in Example 9.
Figure 9:
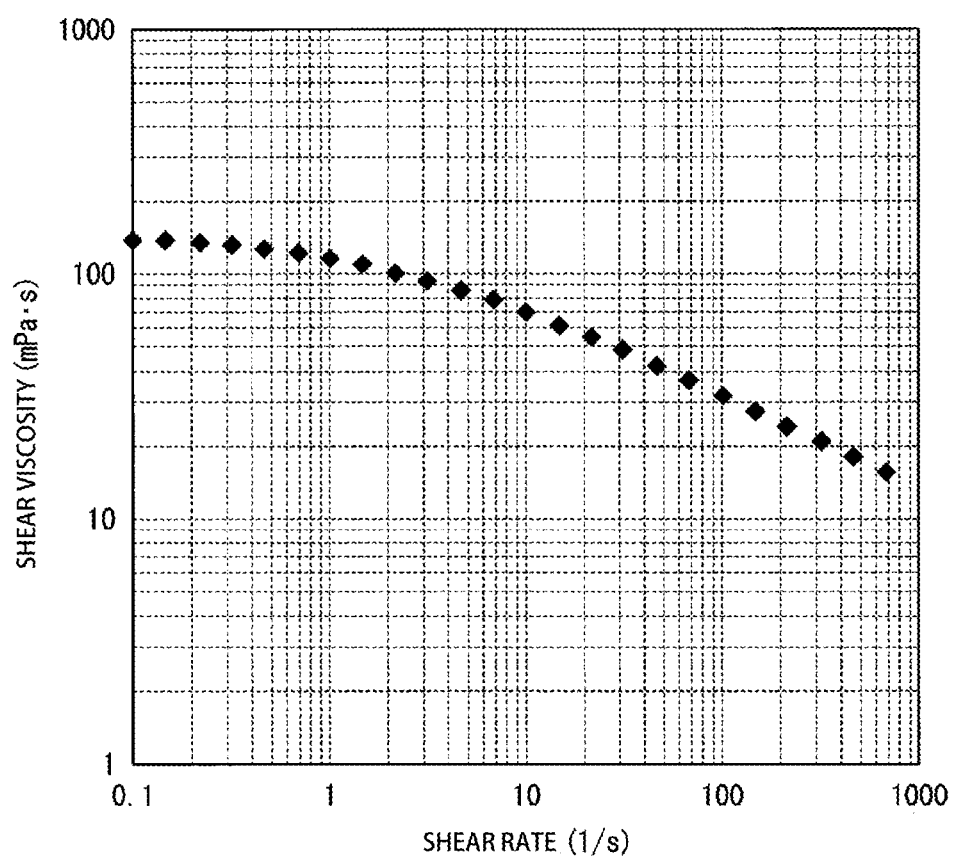
FIG. 9 is a diagram illustrating measurements of static viscoelasticity measured by a rheometer for aqueous dispersion liquid of finely-disintegrated cellulose obtained in Example 9.

1 g of the oxidized pulp obtained through the TEMPO oxidation was dispersed in 99 g of distilled water and micronized for 30 minutes by means of a blender to obtain an aqueous CSNF dispersion liquid at a CSNF concentration of 1%. The CSNF dispersion liquid was put into a quartz cell having a light path length of 1 cm to measure the transmission spectrum by using a spectrophotometer (UV-3600 manufactured by Shimadzu Corporation). The results are shown in FIG. 8. As is apparent from FIG. 8, the aqueous CSNF dispersion liquid showed high transparency. The number average minor axis diameter of CSNF contained in the aqueous CSNF dispersion liquid was 3 nm, and the number average major axis diameter thereof was 1,110 nm. Furthermore, static viscoelasticity was measured by using a rheometer. The results are shown in FIG. 9. As is apparent from FIG. 9, the CSNF dispersion liquid exhibited thixotropic properties.

(Step 2B: Step of Preparing o/w Emulsion)

Next, 1 g of 2,2-azobis-2,4-dimethylvaleronitrile (also termed ADVN hereinafter) as a polymerization initiator was dissolved into 10 g of styrene as a polymerizable monomer. When all the styrene/ADVN mixed solution was added to 40 g of 1% CSNF concentration dispersion liquid, the styrene/ADVN mixed solution and the CSNF dispersion liquid were separated into two layers both with high transparency.

Next, a shaft of an ultrasonic homogenizer was inserted into the mixed liquid that had been separated into two layers, from above the liquid surface of the upper layer, and ultrasonic homogenization was performed for 3 minutes at a frequency of 24 kHz and output of 400 W. After being ultrasonically homogenized, the mixed liquid appeared to be a cloudy emulsion. A droplet of the mixed liquid was dropped onto a glass slide, sealed with a glass cover and observed through an optical microscope. Through the observation, it was confirmed that innumerable emulsion droplets of about 1 µm to several micrometers in size were produced and the droplets were dispersed and stabilized as an o/w emulsion.

(Step 3B: Step of Controlling pH of Emulsion to 3.5 or Less)

Next, an electrode of a pH meter was inserted in the o/w emulsion. pH then was 7. While confirming change of pH, 0.1M hydrochloric acid was dripped into the emulsion to control pH thereof to 3. As a result, the emulsion lost fluidity and formed a gel.

(Step 4A: Step of Obtaining Composite Particles 15 Coated with CNF Through Polymerization Reaction)

The gelled dispersion liquid of the o/w emulsion mentioned above was water-bathed at a temperature of 70° C. for 8 hours to undergo polymerization reaction. After 8 hours, the gel was cooled to room temperature. The gel appeared to remain unchanged before and after the polymerization reaction. When 0.5 M aqueous sodium hydroxide was added to the obtained gel, while the gel was stirred by a stirrer, to control pH thereof to 10.5, the gel fluidity was restored and a dispersion liquid of the polymer was obtained. Furthermore, when the dispersion liquid was centrifuged at a centrifugal force of 75,000 g for 5 minutes, a sediment was obtained. The supernatant was removed by decantation to collect the sediment which was then repeatedly washed using pure water and methanol using a PTFE membrane filter having a pore size of 0.1 µm. The purified and collected substances obtained were redispersed in a solvent at 1% concentration to evaluate the particle size by using a particle size analyzer (NANOTRAC UPA-EX150 manufactured by Nikkiso Co., Ltd.). The average particle size was 4.9 µm. Then, the purified and collected substances were air-dried, followed by vacuum drying at a temperature of 25° C. for 24 hours. As a result, a fine-textured dry powder (composite particles 15) was obtained.

(Shape Observation Through Scanning Electron Microscope)

Figure 10:
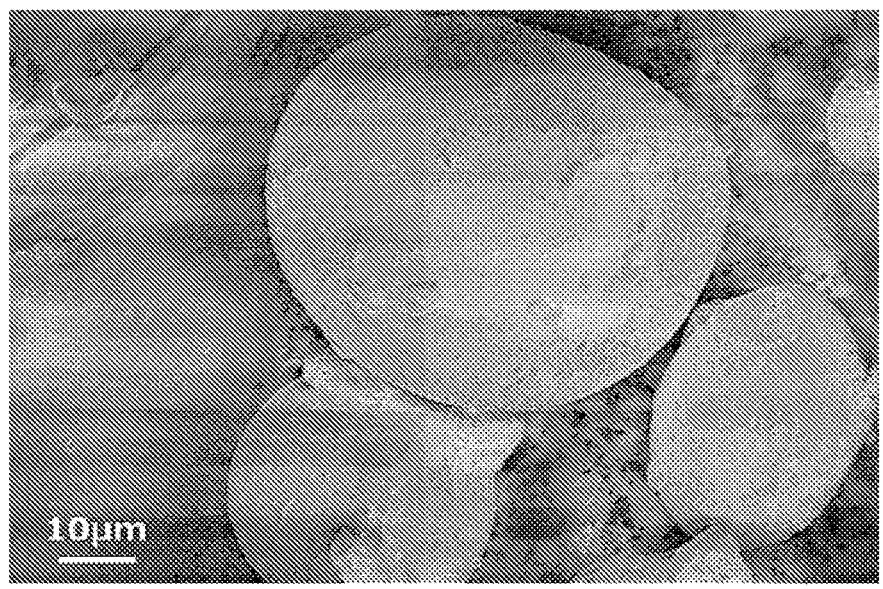
FIG. 10 is a scanning electron microscope (SEM) image of composite particles obtained in Example 9.
Figure 11:
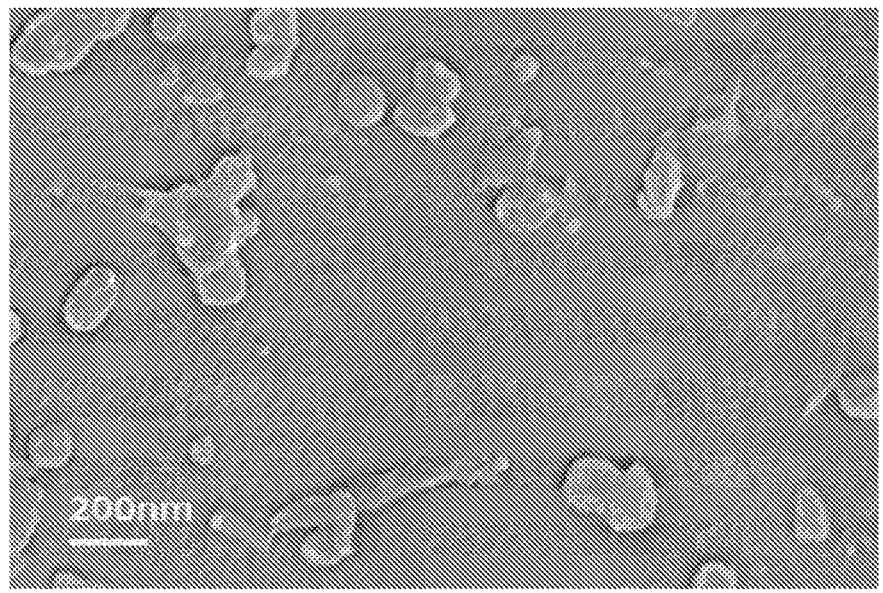
FIG. 11 is a highly magnified scanning electron microscope (SEM) image of composite particles obtained in Example 9.

The obtained dry powder was observed through a scanning electron microscope. The results are shown in FIGS. 10 and 11. As is apparent from FIG. 10, it was confirmed that innumerable granular composite particles 15 were formed, which were derived from the shape of the emulsion droplets, as a result of the polymerization reaction using the o/w emulsion droplets as a template. Furthermore, as shown in FIG. 11, it was confirmed that the surfaces of the composite particles 15 were uniformly coated with CNF having a width of several nanometers. In spite of being repeatedly washed by filtration washing, surfaces of the composite particles 15 were uniformly coated with CNF1, which meant that the monomer inside the composite particles and CNF were in an inseparable state.

(Content of CNF in Composite Particles 15)

The obtained dry powder was weighed and then dispersed in toluene to dissolve polystyrene in the composite particles 15 into toluene. In this case, CNF did not disperse in toluene but precipitated as aggregate. The precipitated CNF aggregate was centrifuged and collected and then vacuum dried at 25° C. for 24 hours, followed by weighing. The weight of the CNF aggregate corresponded to 5% of the dry powder dispersed in toluene. Thus, it was confirmed that the weight ratio of CNF contained in the dry powder of composite particles 15 was 5%.

(Preparation of Molding Resin Composition)

As a thermoplastic resin for kneading, polystyrene (also termed PS hereinafter) pellets (polystyrene pellets for experimental use manufactured by Sanplatec Co., Ltd.) were used. 50 parts by mass PS pellets were mixed with 50 parts by mass dry powder of the composite particles 15 and kneaded by using a twin-screw kneader (Laboplastomill manufactured by Toyo Seiki Seisakusho). The kneading temperature was 200° C. and the screw speed of kneading was 10 rpm. The obtained thermoplastic resin composition was extruded into a string and immersed in cooling water, followed by cutting to pellets again. Through the processing described above, a thermoplastic resin composition was obtained in which a micronized-cellulose composite was dispersed in polystyrene as a thermoplastic resin.

(Preparation of Extruded Film)

Using the pellets of thermoplastic resin composition prepared above as a master batch, an extruded film was prepared. As mentioned in the above section, a Laboplastomill was used for forming an extruded film. The resin discharged from the Laboplastomill was taken up in the form of a film, under tension, by using a film take-up unit dedicated to the Laboplastomill. In the present example, the pellets of thermoplastic composition prepared above were used as a master batch. Specifically, 50 parts by mass PS pellets were mixed with 50 parts by mass master batch and the mixture was used as a material for a film. The kneading temperature was 200° C. and the screw speed of kneading was 20 rpm. CNF dispersibility of the obtained film was evaluated according to the following criteria.

A: No CNF aggregate was visually observed in the film.
B: CNF aggregate was visually observed in the film.

This film was cut to 15 mm×50 mm as a specimen and subjected to a tensile strength test. Specifically, strength (maximum stress) and strain during tension of the film were detected by using a small desktop testing machine (EZ-LX manufactured by Shimadzu Corporation).

Example 10

Composite particles 15 were prepared under the same conditions as in Example 9 except that, without controlling pH in steps 3B and 4B, the emulsion system was bubbled with nitrogen in step 3C, followed by polymerization reaction in step 4C, with the oxygen-free condition being maintained. The composite particles 15 were evaluated as in Example 9.

Example 11

Composite particles 15 were prepared under the same conditions as in Example 9 except that 2,2-azobis-isobutyronitrile (also termed AIBN hereinafter) was used instead of ADVN. The composite particles 15 were evaluated as in Example 9.

Example 12

Composite particles 15 were prepared under the same conditions as in Example 9 except that a carboxymethylated (also termed C-methylated hereinafter) CNF dispersion liquid was used. This C-methylated CNF dispersion liquid was obtained according to the carboxymethylation, instead of TEMPO oxidation, disclosed in Patent Document 2. The composite particles 15 were evaluated as in Example 9.

Example 13

Composite particles 15 were prepared under the same conditions as in Example 9 except that a phosphate esterified CNF dispersion liquid was used. This phosphate esterified CNF dispersion liquid was obtained according to the phosphate esterification, instead of TEMPO oxidation, disclosed in Non-Patent Document 1. The composite particles 15 were evaluated as in Example 9.

Comparative Example 4

An extruded film was formed using 100 parts by mass PS pellets without using the composite particles 15 of Example 9. The rest was prepared as in Example 9 and evaluations were conducted as in Example 9.

Comparative Example 5

Dry powders and film were prepared under the same conditions as in Example 9 except that the CNF dispersion liquid obtained in step 1B of Example 9 was frozen and dried, the obtained dry material was frozen and crushed, and 97.5 parts by mass PS resin were mixed with the obtained 2.5 parts by mass dry powder, for use as a master batch in the process of molding resin composition. The rest was prepared as in Example 9 and evaluations were conducted as in Example 9.

The examples and comparative examples set forth above were evaluated as shown in the following Table 2.

TABLE 2

| | Dispersibility of CNF | Maximum stress (N/mm$^2$) | Strain (%) |
|---|---|---|---|
| Example 9 | A | 58 | 1.7 |
| Example 10 | A | 60 | 1.6 |
| Example 11 | A | 59 | 1.7 |
| Example 12 | A | 55 | 2.2 |
| Example 13 | A | 61 | 1.6 |
| Comparative Example 4 | No CNF used | 30 | 2.7 |
| Comparative Example 5 | B | 27 | 0.8 |

As is apparent from the evaluations of Examples 9 to 13 in Table 2, it was confirmed that, irrespective of the types of finely-disintegrated cellulose 11 (TEMPO oxidized CNF, C-methylated CNF or phosphate esterified CNF) or the types of initiator, an extruded film of CNF/PS resin composite could be prepared from a master batch that had been obtained by kneading a dry powder comprising the composite particles 15 with PS resin pellets, and it was confirmed that, in the film, visually unobservable CNF was dispersed in the PS resin. From the tensile tests of Examples 9 to 13 and Comparative Example 4, it was confirmed that the resin-reinforcing effect of CNF was exerted due to the CNF being dispersed in the resin, and that tensile strength had been improved.

In Comparative Example 5, PS resin pellets and CNF were kneaded at the same ratio as in Example 9; however, aggregate of the CNF was observed in the obtained excluded film and no resin-reinforcing effect of CNF was confirmed. This is considered to be because, in Comparative Example 5, CNF alone was used as a dry material for kneading and thus the CNF fibers strongly aggregated together, and even when the CNF was subjected to kneading together with the PS resin pellets, mixing did not progress. In Examples 9 to 13, composite particles 15 were prepared and these composite particles 15 were used as a dry material for kneading. Therefore, CNF and PS resin formed a composite in microsize order prior to kneading, and accordingly, when the dried composite particles 15 were directly kneaded with PS pellets, the compounding progressed even more. As a result, molding of a composite in which the CNF and the PS resin were uniformly kneaded was finally obtained, i.e., the resin-reinforcing effect of CNF was sufficiently exerted.

INDUSTRIAL APPLICABILITY

The composite particles of the above embodiments can provide advantageous effects from the perspectives of industrial implementation, including improvement of addition efficiency as an additive or kneading efficiency for a resin, or improvement of transportation efficiency, or prevention of decomposition. According to the metal-carrying composite particles as an aspect of the composite particles of the above embodiments, metal nanoparticles can be redispersed without forming aggregate, the LSPR waveform does not change before and after drying, and LSPR can be maintained for the dry powder. The present composite particles can be applied to colorants, adsorbents, cosmetic pigments, sustained-release materials, deodorants, antimicrobial medical materials, antimicrobial items for personal care products, packaging materials, dye-sensitized solar cells, photoelectric conversion materials, photothermal conversion materials, heat shielding materials, optical filters, Raman enhancement elements, image display elements, magnetic powders, catalyst carriers, drug delivery systems or the like, by taking advantage of the characteristics of the finely-disintegrated cellulose on the surfaces of the particles, the metal nanoparticles provided to the finely-disintegrated cellulose and the polymer included in the composite particles.

The composite particles of the above embodiments comprise a thermoplastic resin and cellulose nanofibers, and the dry powder can be obtained through a more easy and simple method. These composite particles can enhance kneading efficiency for a resin and can provide advantageous effects from the perspectives of industrial implementation. In the resin molding prepared using the present composite particles, cellulose nanofibers are favorably dispersed in a resin. Accordingly, the resin molding is expected to be industrially used as resin molding for improving mechanical strength or thermal dimensional stability.

REFERENCE SIGNS LIST 1, 11 Cellulose nanofibers (finely-disintegrated cellulose); 2, 12 Monomer droplet; 3, 13 Polymer particles; 4, 14 Dispersion liquid; 5, 5B, 5C, 15 Composite particles.

What is claimed is:

1. Composite particles, comprising:
   at least one type of polymer particles having surfaces that have thereon coatings formed of finely-disintegrated cellulose,
   wherein the at least one type of polymer particles and the finely-disintegrated cellulose are inseparably bonded together, wherein
   the coatings comprise a functional component other than cellulose;
   the functional component is metal microparticles;
   the metal microparticles and the finely-disintegrated cellulose are inseparably bonded together; and,
   the metal microparticles comprise (a) at least one metal selected from the group consisting of gold, silver, platinum and palladium or (b) a compound of the at least one metal.
2. The composite particles of claim 1, wherein the finely-disintegrated cellulose has crystal surfaces to which an anionic functional group has been introduced.
3. The composite particles of claim 1, wherein the at least one type of polymer particles are obtained by polymerizing a monomer having a vinyl group.
4. The composite particles of claim 1, wherein the at least one type of polymer particles are obtained by polymerizing a monomer having a (meth)acrylic group.
5. The composite particles of claim 1, wherein the at least one type of polymer particles are obtained by polymerizing a polyfunctional monomer having at least two polymerizable functional groups.
6. The composite particles of claim 5, wherein at least one of the at least two polymerizable functional groups of the polyfunctional monomer is a vinyl group.
7. The composite particles of claim 5, wherein at least one of the at least two polymerizable functional groups of the polyfunctional monomer is a (meth)acrylic group.
8. The composite particles of claim 6, wherein the polyfunctional monomer is divinylbenzene.
9. A method of producing composite particles, comprising the steps of:
   a step 1A of defibrating raw cellulose materials in a solvent to obtain a dispersion liquid of finely-disintegrated cellulose;
   a step 2A of coating surfaces of polymerizable monomer droplets with the finely-disintegrated cellulose in the dispersion liquid to achieve stability as an emulsion;
   a step 3A of polymerizing the polymerizable monomer droplets to obtain composite particles in which polymer particles are coated with the finely-disintegrated cellulose;
   a step 4A of providing a functional component other than cellulose to the finely-disintegrated cellulose on the surfaces of the composite particles, wherein the step 4A comprises:
   a step of mixing the dispersion liquid with a solution comprising at least one type of metal ions to obtain a mixed solution; and
   a step of reducing the metal ions in the mixed solution to produce metal microparticles of at least one metal or a compound thereof, while compounding the metal microparticles with the finely-disintegrated cellulose on the surfaces of the composite particles.
10. A method of producing composite particles, comprising the steps of:
    a step 1A of defibrating raw cellulose materials in a solvent to obtain a dispersion liquid of finely-disintegrated cellulose;
    an auxiliary step 1A of compounding a functional component other than cellulose with the finely-disintegrated cellulose in the dispersion liquid;
    a step 2A of coating surfaces of polymerizable monomer droplets with the finely-disintegrated cellulose in the dispersion liquid to achieve stability as an emulsion; and,
    a step 3A of polymerizing the polymerizable monomer droplets to obtain composite particles in which polymer particles are coated with the finely-disintegrated cellulose wherein the auxiliary step 1A comprises:
    a step of mixing the dispersion liquid with a solution comprising at least one type of metal ions to obtain a mixed solution; and
    a step of reducing the metal ions in the mixed solution to produce metal microparticles of at least one metal or a compound thereof, while compounding the metal microparticles with the finely-disintegrated cellulose.
11. A dry powder comprising the composite particles of claim 1 and having a solid content of 80% or more and 100% or less.
12. The composite particles of claim 1, wherein the at least one type of polymer particles comprises particles formed of a thermoplastic polymer.
13. The composite particles of claim 12, wherein the finely-disintegrated cellulose has crystal surfaces to which an anionic functional group has been introduced.
14. The composite particles of claim 12, wherein the at least one type of polymer particles are obtained by polymerizing a monomer having a vinyl group.
15. The composite particles of claim 12, wherein the at least one type of polymer particles are obtained by polymerizing a monomer having a (meth)acrylic group.
16. The composite particles of claim 12, wherein the at least one type of polymer particles are obtained by polymerizing a monofunctional monomer having only one polymerizable functional group.
17. The composite particles of claim 16, wherein the monofunctional monomer is styrene.
18. A method of producing composite particles, comprising the steps of:
    a step 1B of defibrating raw cellulose materials in a solvent to obtain a dispersion liquid of finely-disintegrated cellulose;

a step 2B of coating surfaces of polymerizable monomer droplets with the finely-disintegrated cellulose in the dispersion liquid to achieve stability as an emulsion;

a step 3B of controlling pH of the emulsion to 3.5 or less; and a step 4B of polymerizing the polymerizable monomer droplets in the emulsion to obtain composite particles in which polymer particles are coated with the finely-disintegrated cellulose.

19. The method of producing composite particles of claim 18, wherein the pH of the emulsion is controlled to 10 or more in the step 4B.

20. A method of producing composite particles, comprising the steps of:

a step 1B of defibrating raw cellulose materials in a solvent to obtain a dispersion liquid of finely-disintegrated cellulose;

a step 2B of coating surfaces of polymerizable monomer droplets with the finely-disintegrated cellulose in the dispersion liquid to achieve stability as an emulsion;

a step 3C of deoxygenating a system of the emulsion; and a step 4C of polymerizing the polymerizable monomer droplets in the emulsion, while maintaining a state of the system being deoxygenated, to obtain composite particles in which polymer particles are coated with the finely-disintegrated cellulose.

21. A molding resin composition comprising the composite particles of claim 12 and having a solid content of 80% or more.

* * * * *